United States Patent
Smith et al.

(10) Patent No.: US 6,861,458 B2
(45) Date of Patent: Mar. 1, 2005

(54) PHOTOPROTECTIVE AND LIGHTFASTNESS-ENHANCING SILOXANES

(75) Inventors: Thomas W. Smith, Penfield, NY (US); Kathleen M. McGrane, Webster, NY (US)

(73) Assignee: Xerox Corporation, Stamford, CT (US)

( * ) Notice: Subject to any disclaimer, the term of this patent is extended or adjusted under 35 U.S.C. 154(b) by 89 days.

(21) Appl. No.: 10/001,572

(22) Filed: Nov. 15, 2001

(65) Prior Publication Data

US 2003/0133886 A1 Jul. 17, 2003

(51) Int. Cl.$^7$ .......................... C08G 77/14; C09D 11/10
(52) U.S. Cl. ....................... 523/160; 524/860; 524/862; 524/869; 424/43
(58) Field of Search .................... 424/43; 524/860, 524/862, 869; 523/160

(56) References Cited

U.S. PATENT DOCUMENTS 4,256,493 A    3/1981 Yokoyama et al. ........... 106/22

(List continued on next page.)

FOREIGN PATENT DOCUMENTS

EP            0867486         9/1998

(List continued on next page.)

OTHER PUBLICATIONS

Copending U.S. Appl. No., filed concurrently herewith, entitled "Aqueous Inks Containing Lightfastness–Enhancing Siloxanes," by Thomas W. Smith et al.
Copending U.S. Appl. No., filed concurrently herewith, entitled "Recording Sheets with Lightfastness–Enhancing Siloxanes," by Thomas W. Smith et al.

*Primary Examiner*—Kamal Saeed
(74) *Attorney, Agent, or Firm*—Judith L. Byorick

(57) ABSTRACT

Disclosed is a compound of one of the formulae

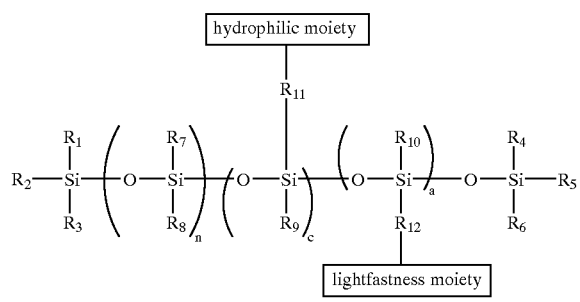
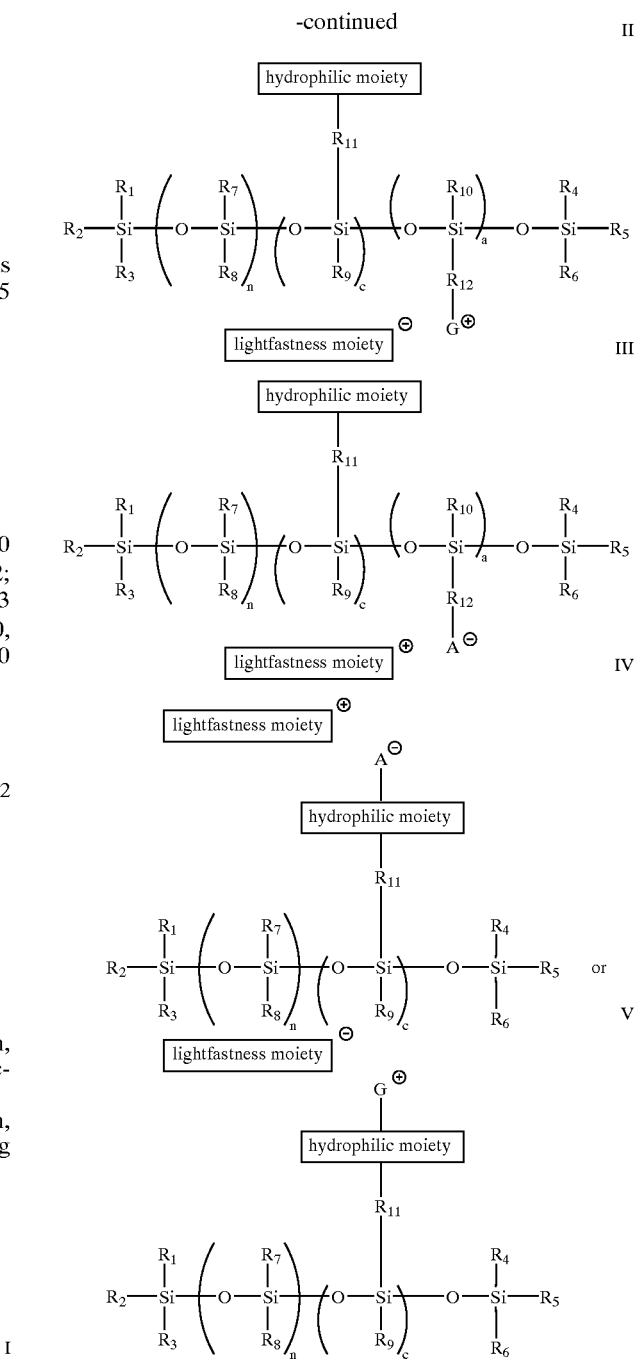

wherein $R_1$, $R_2$, $R_3$, $R_4$, $R_5$, $R_6$, $R_7$, $R_8$, $R_9$, and $R_{10}$ each, independently of the others, is an alkyl group, an aryl group, an arylalkyl group, or an alkylaryl group, $R_{11}$ and $R_{12}$ each, independently of the others, is an alkylene group, an arylene group, an arylalkylene group, or an alkylarylene group, G is a cationic moiety, A is an anionic moiety, n is an integer representing the number of repeat —OSi($R_7$)($R_8$)— monomer units, a is an integer representing the number of repeat —OSi($R_{10}$)($R_{12}$-lightfastness moiety)— monomer units, and c is an integer representing the number of repeat —OSi($R_9$)($R_{11}$-hydrophilic moiety)— monomer units.

14 Claims, No Drawings

U.S. PATENT DOCUMENTS

| | | | |
|---|---|---|---|
| 4,859,759 A | 8/1989 | Maycock et al. | 528/27 |
| 5,051,458 A | 9/1991 | Costanzi et al. | 524/99 |
| 5,089,250 A | 2/1992 | Forestier et al. | 424/43 |
| 5,102,707 A | 4/1992 | Canivenc et al. | 428/44 |
| 5,270,426 A | 12/1993 | Sakuta et al. | 528/15 |
| 5,466,768 A | 11/1995 | Yang | 528/15 |
| 5,610,257 A | 3/1997 | Richard et al. | 528/15 |
| 5,643,356 A | 7/1997 | Nohr et al. | 106/31.49 |
| 5,686,633 A | 11/1997 | Vieira et al. | 549/434 |
| 5,719,204 A | 2/1998 | Beach et al. | 523/161 |
| 5,837,792 A | 11/1998 | Meuwly et al. | 528/27 |
| 6,087,416 A | 7/2000 | Pearlstine et al. | 523/160 |
| 6,106,599 A | 8/2000 | Breton et al. | 106/31.29 |
| 6,124,376 A | 9/2000 | Nichols et al. | 523/160 |
| 6,142,618 A | 11/2000 | Smith et al. | 347/85 |
| 6,200,369 B1 | 3/2001 | Schwarz | 106/31.43 |
| 6,231,655 B1 | 5/2001 | Marritt | 106/31.58 |
| 6,245,138 B1 | 6/2001 | Nyssen et al. | 106/31.86 |
| 6,270,214 B1 | 8/2001 | Smith et al. | 347/101 |
| 6,569,511 B1 | 5/2003 | Smith et al. | 428/195 |

FOREIGN PATENT DOCUMENTS

| | | |
|---|---|---|
| EP | 1 221 381 A2 | 7/2002 |
| JP | 10007958 | 1/1998 |
| JP | 10007969 | 1/1998 |
| JP | 10-278435 | 10/1998 |
| JP | 11-099740 | 4/1999 |
| JP | 2000-141875 | 5/2000 |
| WO | WO 97/20000 | 6/1997 |

PHOTOPROTECTIVE AND LIGHTFASTNESS-ENHANCING SILOXANES

Copending application U.S. Ser. No. 10/001,741 not yet assigned; filed Nov. 15, 2001, entitled "Aqueous Inks Containing Lightfastness-Enhancing Siloxanes," with the named inventors Thomas W. Smith and Kathleen M. McGrane, The disclosure of which is totally incorporated herein by reference, discloses an ink composition which comprises water, a colorant, and a lightfastness agent which is a polysiloxane having thereon a hydrophilic moiety and a lightfastness moiety. Also disclosed are printing processes using the ink.

Application U.S. Ser. No. 10/002,342 No., now U.S. Pat. No. 6,569,511 filed Nov. 15, 2001, entitled "Recording Sheets with Lightfastness-Enhancing Siloxanes," with the named inventors Thomas W. Smith and Kathleen M. McGrane, the disclosure of which is totally incorporated herein by reference, discloses a recording sheet which comprises a substrate and on image-receiving coating situated on at least one surface of the substrate, said image-receiving coating being suitable for receiving images of an aqueous ink, said image-receiving coating comprising a lightfastness agent which is a polysiloxane having thereon a hydrophilic moiety and a lightfastness moiety.

BACKGROUND OF THE INVENTION

The present invention is directed to compositions of matter suitable for use as photoprotectants or lightfastness enhancing agents. More specifically, the present invention is directed to oligomeric or polymeric siloxanes having thereon moieties imparting to the oligomers or polymers the ability to function as photoprotectants or lightfastness enhancing agents. One embodiment of the present invention is directed to a compound of one of the formulae

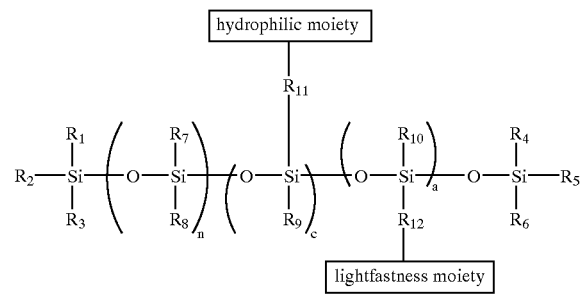

I

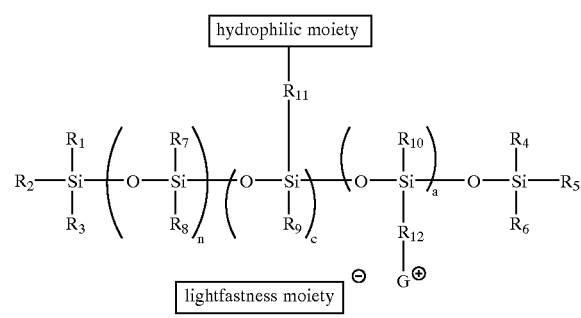

II

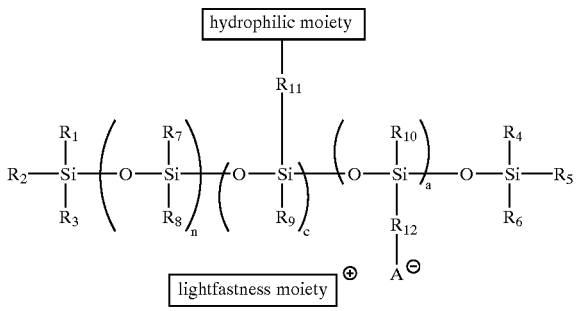

III

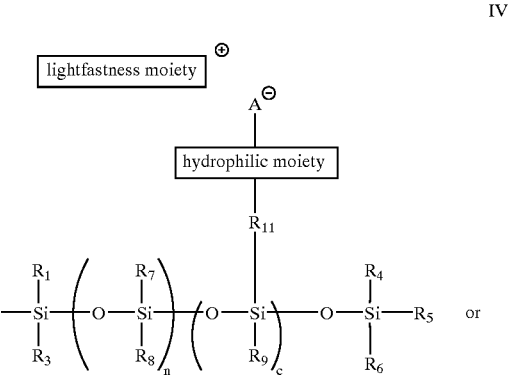

IV

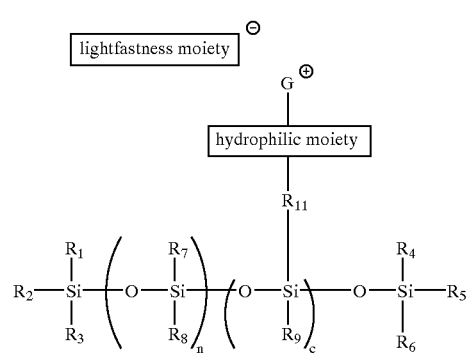

V wherein $R_1$, $R_2$, $R_3$, $R_4$, $R_5$, $R_6$, $R_7$, $R_8$, $R_9$, and $R_{10}$ each, independently of the others, is an alkyl group, an aryl group, an arylalkyl group, or an alkylaryl group, $R_{11}$ and $R_{12}$ each, independently of the others, is an alkylene group, an arylene group, an arylalkylene group, or an alkylarylene group, G is a cationic moiety, A is an anionic moiety, n is an integer representing the number of repeat —OSi($R_7$)($R_8$)— monomer units, a is an integer representing the number of repeat —OSi($R_{10}$)($R_{12}$-lightfastness moiety)— monomer units, and c is an integer representing the number of repeat —OSi($R_9$)($R_{11}$-hydrophilic moiety)— monomer units.

Compositions for photoprotection of the skin and/or hair against ultraviolet radiation are known for use in sunscreens, cosmetics, hair products, and the like. Examples of such materials include aromatic compounds such as p-aminobenzoic acid derivatives, benzylidenecamphor derivatives, cinnamic acid derivatives, benzotriazole derivatives, and the like.

U.S. Pat. No. 6,270,214 (Smith et al.), the disclosure of which is totally incorporated herein by reference, discloses a process which comprises (a) applying to a substrate a fixing fluid which comprises a material selected from the group consisting of (1) block or graft copolymers of dialkyl-siloxanes and polar, hydrophilic monomers capable of interacting with an ink colorant to cause the colorant to become complexed, laked, or mordanted, (2) organopolysiloxane copolymers having functional side groups capable of interacting with an ink colorant to cause the colorant to become complexed, laked, or mordanted, (3) perfluorinated polyalkoxy polymers, (4) perfluoroalkyl surfactants having thereon at least one group capable of interacting with an ink colorant to cause the colorant to become complexed, laked, or mordanted, and (5) mixtures thereof; (b) incorporating into an ink jet printing apparatus an ink composition which comprises water and a colorant which becomes complexed, laked, or mordanted upon contacting the fixing fluid; and (c) causing droplets of the ink composition to be ejected in an imagewise pattern onto the substrate.

U.S. Pat. No. 6,142,618 (Smith et al.), the disclosure of which is totally incorporated herein by reference, discloses a fluid deposition apparatus comprising (a) a fluid supply, (b) a porous fluid distribution member in operative connection with the fluid supply, enabling wetting of the fluid distribution member with a fluid, and (c) a porous metering membrane situated on the fluid distribution member, whereby the metering membrane enables uniform metering of the fluid from the fluid distribution member onto a substrate.

U.S. Pat. No. 6,124,376 (Nichols et al.), the disclosure of which is totally incorporated herein by reference, discloses a process which comprises incorporating into an ink jet printing apparatus an ink composition which comprises water, a colorant, and a polymer of the formula

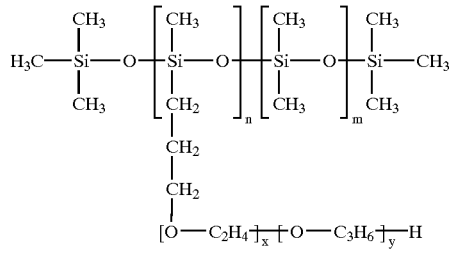

wherein m, n, x, and y are each integers representing the number of repeat monomer units, and wherein the ratio of x:y is from about 10:90 to about 90:10, and causing droplets of the ink to be ejected in an imagewise pattern onto a recording sheet.

U.S. Pat. No. 6,200,369 (Schwarz), the disclosure of which is totally incorporated herein by reference, discloses an ink composition which comprises (a) water, (b) a colorant, and (c) an additive selected from the group consisting of diamido quaternary dialkyl ammonium salts, bitail quaternary tetraalkyl ammonium salts, bitail imidazolium salts, bitail biomimetic phospholipid salts, specific bisquaternary salts, β-hydroxyethyl ethylene diamine fatty acids, specific polyammonium salts, ethoxylated polyamine compounds, biquaternary pyridinium salts, aminofunctional polyorganosiloxanes, and mixtures thereof.

U.S. Pat. No. 6,106,599 (Breton et al.), the disclosure of which is totally incorporated herein by reference, discloses an ink composition comprising (1) an azole compound, (2) a viscosity compound, (3) a lightfastness component, (4) an antioxidant, and (5) a colorant.

U.S. Pat. No. 5,719,204 (Beach et al.), the disclosure of which is totally incorporated herein by reference, discloses polymeric dispersants used in formulating aqueous ink compositions, as well as inks containing those dispersants. The dispersants are graft copolymers comprising a hydrophilic polymeric segment, a hydrophobic polymeric segment incorporating a hydrolytically-stable siloxyl substituent, and a stabilizing segment, such as a reactive surfactant macromer, a protective colloid macromer, or a non-siloxyl hydrophobic monomer. The inks made with these dispersants show excellent stability, print characteristics, waterfastness, light-fastness, optical density, and in-use maintenance characteristics.

U.S. Pat. No. 5,686,633 (Vieira et al.), the disclosure of which is totally incorporated herein by reference, discloses a recording material for ink jet printing comprising a carrier having a surface which can be printed on or a carrier coated on one side with a material which can be printed on, wherein the carrier or the coating contains as a stabilizer at least one compound of the formula

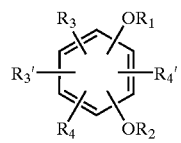

in which $R_1$ and $R_2$ independently of one another are $C_1$–$C_4$ alkyl which is unsubstituted or substituted by one or two —OH, —COO$^-$M$^+$ and/or —SO$_3$$^-$M$^+$ groups, $C_3$–$C_5$ alkenyl, $C_3$–$C_5$ alkynyl,

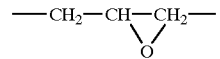

—CH$_2$CH(OH)CH$_2$—SO$_3$$^-$M$^+$, —CO-alkyl($C_1$–$C_4$) which is unsubstituted or substituted by —COOR$^o$ or —CO—N($R_5$)($R_6$) or, if OR$_1$ and OR$_2$ are in the ortho position relative to one another, $R_1$ and $R_2$ together are $C_1$–$C_6$ alkylene, M$^+$ being H$^+$, a monovalent, divalent or trivalent metal cation or a group ($R_{12}$')N$^+$($R_{12}$")($R_{13}$')($R_{14}$'), wherein $R_{12}$', $R_{12}$", $R_{13}$ and $R_{14}$ independently of one another are H, $C_1$–$C_4$ alkyl which is unsubstituted or substituted by 1 or 3 OH, $C_1$–$C_4$ alkyl interrupted by O, allyl, cyclopentyl, cyclohexyl, phenyl, benzyl or tolyl, or $R_1$ is a group

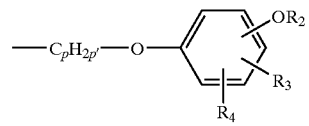

in which p' is a number from 2 to 6, $R_5$ and $R_6$ independently of one another are H or $C_1$–$C_4$ alkyl which is unsubstituted or substituted by an OH, COOR$^o$, —COO$^-$M$^+$, SO$_3$$^-$M$^+$, P(O)(O-M$^+$)$_2$ or P(O)(OR$^o$)$_2$ group, $R_3$' and $R_4$' independently of one another are H, $C_1$–$C_4$ alkyl, OH or $C_1$–$C_4$ alkoxy, $R_3$ and $R_4$ independently of one another are H, halogen, —OR$_7$, —COOR$^o$, —COO$^-$M+, —OOC—R$_5$, —CO—N($R_5$)($R_6$), —($R_5$)N—CO—$R_6$, —CO—$R_5$, —SO$_3$$^-$M$^+$, —SO$_2$N($R_5$)($R_6$), P(OR$_5$)$_3$, —(O)P—(O-M$^+$)$_2$, —(O)P—(OR$^o$)$_2$, $C_1$–$C_8$ alkyl which is unsubstituted or substituted by 1 to 7 —OR$_5$ or —OO—C—$R_5$ groups, by 1 or 2 —COOR$^o$, —COO-M$^+$, or —CO—N($R_5$)($R_6$) groups or by one or two —SO$_3$$^-$M$^+$, —SO$_2$N($R_5$)($R_6$) or —(O)P—(OR$^o$)$_2$ or —(O)P(O-M$^+$)$_2$ groups, where M$^+$, $R_5$ and $R_6$ are as defined above, or $C_5$–$C_6$ cycloalkyl or allyl, R$^o$ being $C_1$–$C_4$ alkyl which is unsubstituted or substituted by an —OH group or —(CH$_2$CH$_2$O)$_r$—H in which r is 1 to 12, and $R_7$ being $C_1$–$C_4$ alkyl or —CO-alkyl($C_1$–$C_4$) each of which is unsubstituted or substituted by 1 or 2 —OH groups or $R_3$ and $R_4$ independently of one another are one of the groups

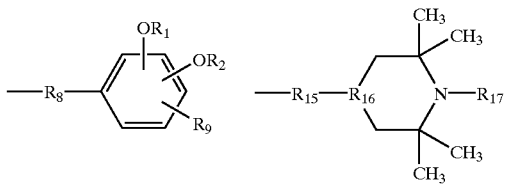

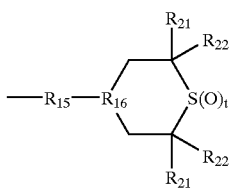

in which $R_8$ is a direct bond or methylene, $R_9$ is H, $C_1$–$C_8$ alkyl, —COO$^-$M$^+$ or —SO$_3^-$M$^+$, where M$^+$, $R_1$ and $R_2$ are as defined above, $R_{15}$ is —CO—, —(O)$_g$—C$_p$H$_{2p}$—CO—, —OOC—C$_p$H$_{2p}$—, —COO—C$_p$H$_{2p}$—, —O—CH$_2$CH(OH)—CH$_2$— or

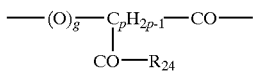

in which g is 0 or 1 and p is 1 to 6 and $R_{24}$ is —OR$_5$, —N(R$_5$)(R$_6$) or a group

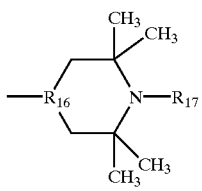

and $R_{16}$ is one of the following radicals:

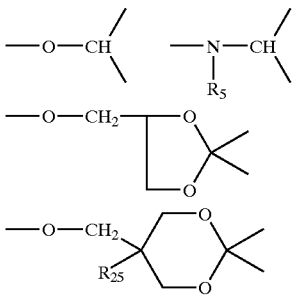

in which $R_{25}$ is H or $C_1$–$C_4$ alkyl, $R_{17}$ is H, $C_1$–$C_4$ alkyl which is unsubstituted or substituted by an —OH group, —CH$_2$—CH(OH)—CH$_2$—OH, $C_1$–$C_4$ alkoxy, —OH, —CO-alkyl($C_1$–$C_4$), —COCH=CH$_2$, allyl, benzyl or a group

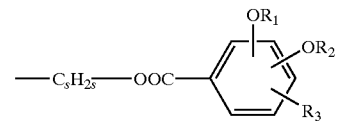

in which s is the number 2 or 3, t is a number from 0 to 2 and $R_{21}$ and $R_{22}$ independently of one another are H, $C_1$–$C_4$ alkyl or phenyl.

U.S. Pat. No. 5,643,356 (Nohr et al.), the disclosure of which is totally incorporated herein by reference, discloses an improved ink suitable for ink jet printing comprising a mixture of a colorant, an arylketoalkene stabilizing compound or a photoreactor, and a liquid vehicle, wherein the colorant is light-stable. When the photoreactor is combined with a wavelength-selective sensitizer to form a radiation transorber, the colorant is mutable upon exposure of the radiation transorber to specific, narrow bandwidth radiation. The colored composition may also contain a molecular includant having a chemical structure which defines at least one cavity wherein each of the colorant and photoreactor or radiation transorber is associated with the molecular includant. The invention also includes ink jet print cartridges containing the improved ink, ink jet printers containing the improved ink and methods of printing using the improved ink.

U.S. Pat. No. 5,610,257 (Richard et al.), the disclosure of which is totally incorporated herein by reference, discloses topically applicable sunscreen/cosmetic compositions well suited for enhanced photoprotection of human skin and/or hair against the damaging effects of UV-A and UV-B irradiation, particularly solar radiation, which comprise a photoprotecting effective amount of a novel benzotriazole-substituted polyorganosiloxane/polyorganosilane having one of the formulae (1) to (3):

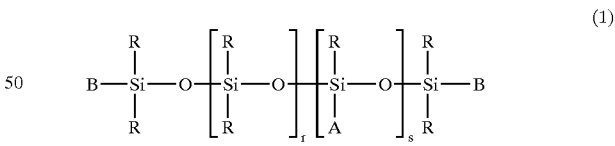
(1)

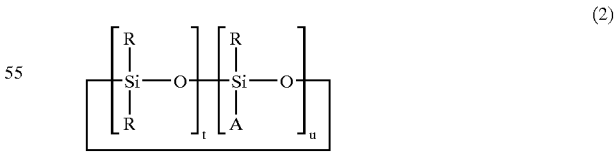
(2)

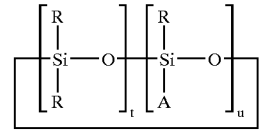
(3)

wherein A is a monovalent benzotriazole radical which comprises an acrylate or acrylamide functional group, which is bonded directly to a silicon atom, and which has the formula (4):

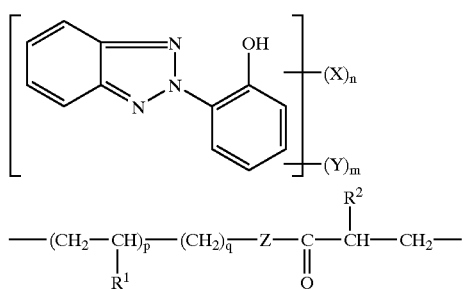

U.S. Pat. No. 5,089,250 (Forestier et al.), the disclosure of which is totally incorporated herein by reference, discloses the cosmetic use, in particular for use as a UV filter, of benzotriazole diorganopolysiloxanes having either formula:

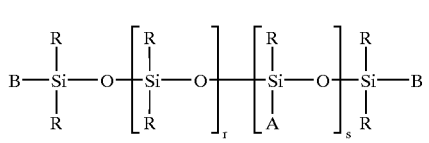

where R is $C_1$–$C_{10}$ alkyl, phenyl, or 3,3,3-trifluoropropyl, B is R or A, r=0–200, s=0–50, or formulas:

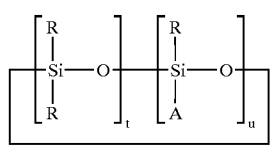

where u=1–20, t=0–20 and t+u≧3. A and/or B represent a benzotriazole $C_3$–$C_{12}$ alkylene which may be substituted.

U.S. Pat. No. 4,256,493 (Yokoyama et al,), the disclosure of which is totally incorporated herein by reference, discloses a jet ink composition which comprises an aqueous jet ink containing a water-soluble dye, a wetting agent, and water as main components and, incorporated therein, a water-soluble ultraviolet absorbing agent as well as a metal salt, when necessary.

PCT Application WO 97/20000 (Nohr et al.), the disclosure of which is totally incorporated herein by reference, discloses colorant stabilizers and a colorant composition which includes a colorant and a colorant stabilizer. The colorant stabilizer imparts light stability to the colorant so that the colorant does not fade when exposed to electromagnetic radiation such as sunlight or artificial light.

European Patent Application EP 0867486 (Gangal et al.), the disclosure of which is totally incorporated herein by reference, discloses a jet printing ink composition which results in reduced drop misdirection and missing nozzles. The aqueous-based ink composition includes at least one colorant, a wetting agent; and a co-solvent comprising a substituted or unsubstituted lactam, an amide, or mixtures thereof.

Japanese Patent Publication JP 10278435, the disclosure of which is totally incorporated herein by reference, discloses a thermal recording medium having excellent recording traveling properties with excellent light resistance, heat resistance, and chemical resistance of a recorded part and white part. In the thermal recording medium comprising a thermal recording layer containing colorless or pale basic dye, colorant and a protective layer containing an ultraviolet absorbent sequentially provided on a support, the colorant is 1,1-bis(4-hydroxyphenyl)-1-phenylethane and the absorbent is N,N'-bis(2-hydroxy-3-(2H-benzotriazole-2-il)-5-methylbenzyl)-1,4-benzene-dicarboxyamide.

Japanese Patent Publication JP 11099740, the disclosure of which is totally incorporated herein by reference, discloses an ink jet recording sheet having superior light fastness of a recorded image, particularly superior light fastness of a magenta image, and also superior characteristics such as recording density and recording quality. At least one kind of compound like N-2-(3-(benzotriazole-2-yl)-4-hydroxyphenyl propionyl amino)ethyl-N,N,N-trimethyl ammonium chloride and others by a general formula

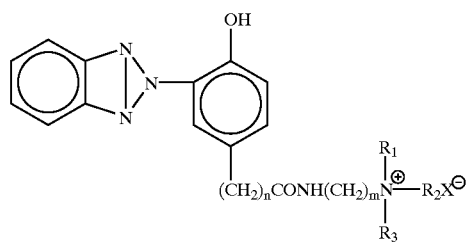

is contained in an ink jet recording sheet for forming a recorded image by using aqueous ink. In the formula, $R_1$, $R_2$, and $R_3$ respectively represent hydrogen atom, $C_1$–$C_4$ alkyl or $C_1$–$C_4$ hydroxyalkyl and X represents organic or inorganic anion. (n) represents 0, 1, or 2 and (m) represents an integer of 2 to 6.

Japanese Patent Publication JP 2000141875, the disclosure of which is totally incorporated herein by reference, discloses a superior ink jet recording sheet of superior light fastness of a recorded image, particularly light fastness of a magenta image and free from the yellowing of surface, the deterioration of the picture quality and the like. A recorded image is formed on an ink jet recording sheet by using an aqueous ink, and in the recording sheet, at least one kind of benzotrizol compound represented by the formula

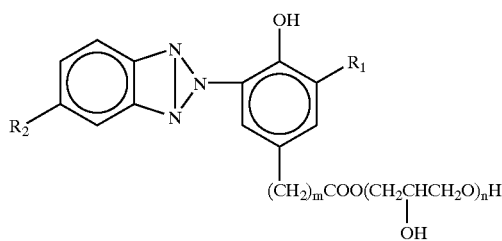

3-(3-(benzotriazol-2-yl)-4-hydroxyphenyl)decaglyceryl propionate or the like is contained in the recording sheet. In the formula, $R_1$ represents a hydrogen atom or a 1–5C alkyl, and $R_2$ represents a hydrogen atom or a chlorine atom. (m) represents 0 or 1–4 integer and (n) represents 1–12 integer.

Japanese Patent Publication JP 10007958, the disclosure of which is totally incorporated herein by reference, discloses an additive for a water based ink which is especially excellent in water resistance and can give a record with a high quality image hardly accompanied by blur of characters or images or border blur at the place where two colors are applied one on top of another. The additive is a polyorganosiloxane-modified amphiphilic polymer which has polyorganosiloxane units and is obtained by copolymerizing a hydrophilic ethylenically unsaturated monomer and a hydrophobic ethylenically unsaturated monomer, or polymerizing an amphiphilic ethylenically unsaturated monomer, in the presence of a polyorganosiloxane having mercaptized organic groups.

Japanese Patent Publication JP 10007969, the disclosure of which is totally incorporated herein by reference, discloses an ink composition excellent in light resistance, water resistance, and water repellency obtained by mixing a compound having a group having the function of stabilizing against ultraviolet rays with a specified amphipathic polymer. The composition is prepared by mixing a polar-solvent-soluble compound having the function of stabilizing against ultraviolet rays (e.g., hydroxyphenylbenzotriazole derivative) with an amphipathic polymer having polyorganosiloxane units, preferably obtained by radical-polymerizing a mixture comprising a hydrophilic ethylenically unsaturated monomer (e.g., acrylamide) and/or an amphipathic ethylenically unsaturated monomer (e.g., methoxypolyethylene glycol monomethacrylate) and optionally a hydrophobic ethylenically unsaturated monomer (e.g., methyl methacrylate) in the presence of an SH-containing polyorganosiloxane.

While known compositions and processes are suitable for their intended purposes, a need remains for improved lightfastness enhancing agents. In addition, a need remains for photoprotective compositions that can be employed in personal care products such as sunblocks, makeup, hair products, or the like.

SUMMARY OF THE INVENTION

The present invention is directed to a compound of one of the formulae

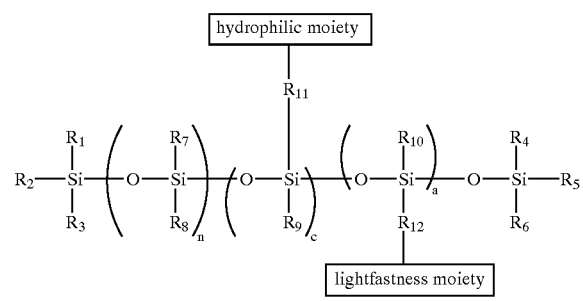

I

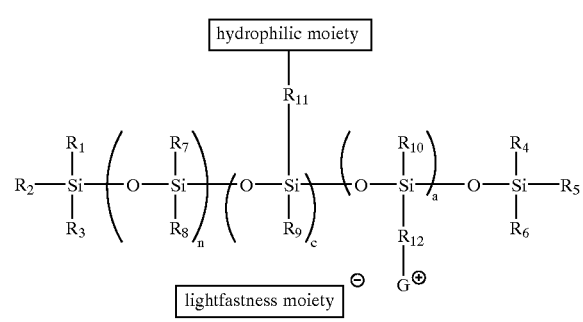

II

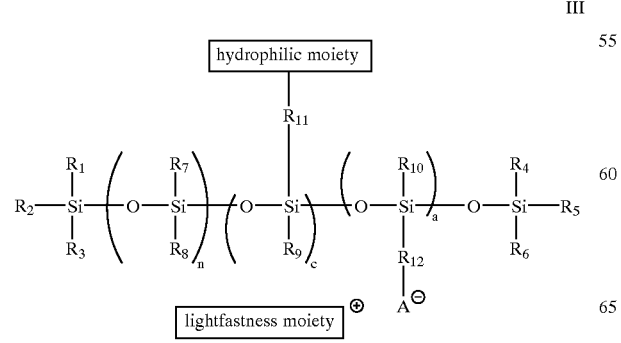

III

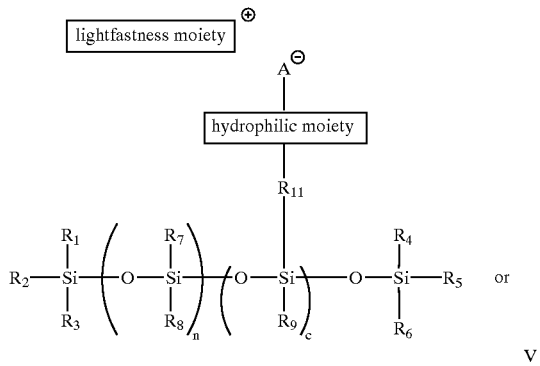

IV or

V wherein $R_1$, $R_2$, $R_3$, $R_4$, $R_5$, $R_6$, $R_7$, $R_8$, $R_9$, and $R_{10}$ each, independently of the others, is an alkyl group, an aryl group, an arylalkyl group, or an alkylaryl group, $R_{11}$ and $R_{12}$ each, independently of the others, is an alkylene group, an arylene group, an arylalkylene group, or an alkylarylene group, G is a cationic moiety, A is an anionic moiety, n is an integer representing the number of repeat —$OSi(R_7)(R_8)$— monomer units, a is an integer representing the number of repeat —$OSi(R_{10})(R_{12}$-lightfastness moiety)— monomer units, and c is an integer representing the number of repeat —$OSi(R_9)(R_{11}$-hydrophilic moiety)— monomer units.

DETAILED DESCRIPTION OF THE INVENTION

The present invention is directed to compounds of one of the formulae

I

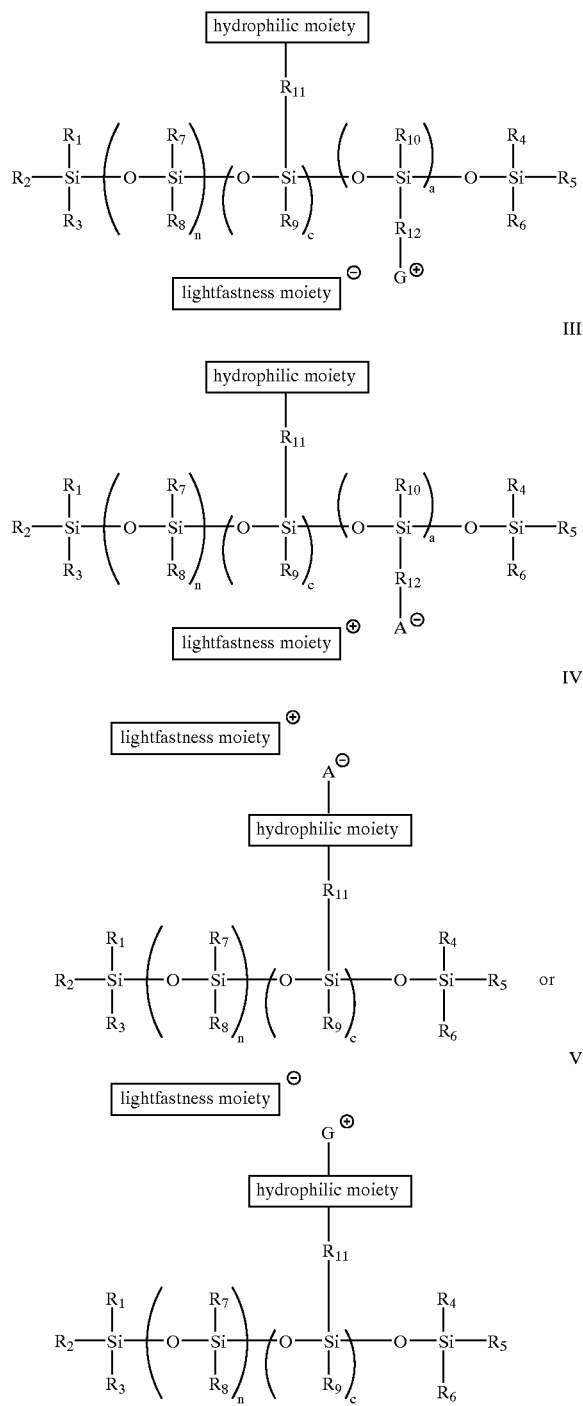

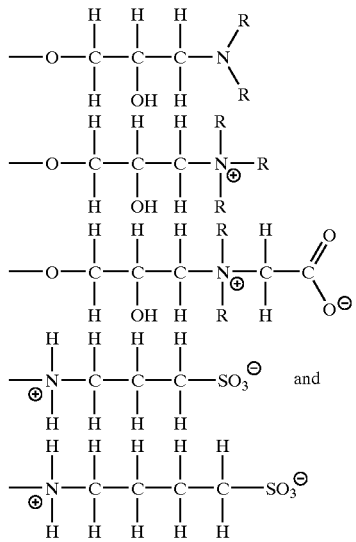

wherein $R_1$, $R_2$, $R_3$, $R_4$, $R_5$, $R_6$, $R_7$, $R_8$, $R_9$, and $R_{10}$ each, independently of the others, is an alkyl group (including linear, branched, cyclic, saturated, unsaturated, and substituted alkyl groups, and wherein hetero atoms, such as oxygen, sulfur, nitrogen, silicon, phosphorus, and the like can be present in the alkyl group), typically with from 1 to about 22 carbons and preferably with from 1 to about 5 carbon atoms, although the number of carbon atoms can be outside of these ranges, an aryl group (including substituted aryl groups), typically with from 6 to about 12 carbon atoms, with 6 carbon atoms being preferred, although the number of carbon atoms can be outside of this range, an arylalkyl group (including substituted arylalkyl groups), typically with from 7 to about 28 carbon atoms, and preferably with from 7 to about 10 carbon atoms, although the number of carbon atoms can be outside of these ranges, or an alkylaryl group (including substituted alkylaryl groups), typically with from 7 to about 28 carbon atoms, and preferably with from 7 to about 10 carbon atoms, although the number of carbon atoms can be outside of these ranges, $R_{11}$ and $R_{12}$ each, independently of the others, is an alkylene group (including linear, branched, cyclic, saturated, unsaturated, and substituted alkylene groups, and wherein hetero atoms, such as oxygen, sulfur, nitrogen, silicon, phosphorus, and the like can be present in the alkylene group), typically with from 1 to about 22 carbons and preferably with from 1 to about 5 carbon atoms, although the number of carbon atoms can be outside of these ranges, an arylene group (including substituted arylene groups), typically with from 6 to about 12 carbon atoms, with 6 carbon atoms being preferred, although the number of carbon atoms can be outside of this range, an arylalkylene group (including substituted arylalkylene groups), typically with from 7 to about 28 carbon atoms, and preferably with from 7 to about 10 carbon atoms, although the number of carbon atoms can be outside of these ranges, or an alkylarylene group (including substituted alkylarylene groups), typically with from 7 to about 28 carbon atoms, and preferably with from 7 to about 10 carbon atoms, although the number of carbon atoms can be outside of these ranges, G is a cationic moiety capable of forming an ionic bond with an anionic lightfastness moiety, such as those of the formula $-NR_{13}R_{14}R_{15}^+$, wherein $R_{13}$, $R_{14}$, and $R_{15}$ each, independently of the others, is a hydrogen atom, an alkyl group (including linear, branched, saturated, unsaturated, cyclic, and substituted alkyl groups, and wherein hetero atoms, such as oxygen, sulfur, nitrogen, silicon, phosphorus, or the like, can be placed between the carbon atoms in the alkyl group), typically with from 1 to about 22 carbon atoms, and preferably with from 1 to about 7 carbon atoms, although the number of carbon atoms can be outside of this range, and wherein two or more of $R_{13}$, $R_{14}$, and $R_{15}$ can be joined together to form a ring, or the like, with specific examples of cationic groups $-G^+$ and substituents $-R_{12}G^+$ including (but not being limited to)

wherein each R, independently of the others, is a hydrogen atom, an alkyl group, including linear, branched, cyclic, substituted, and unsaturated alkyl groups, typically with from 1 to about 22 carbons and preferably with from 1 to about 7 carbon atoms, although the number of carbon atoms can be outside of these ranges, and wherein in a specific embodiment, the R groups are all methyl groups, A is an anionic moiety, such as

—COOH

—COO⁻

—OH

—O—

—SO₃H

—SO₃⁻ or the like, wherein the substituents on the substituted alkyl, alkylene, aryl, arylene, arylalkyl, arylalkylene, alkylaryl, and alkylarylene groups can be (but are not limited to) hydroxy groups, amine groups, ammonium groups, cyano groups, pyridine groups, pyridinium groups, ether groups, aldehyde groups, ketone groups, ester groups, amide groups, carbonyl groups, sulfide groups, sulfoxide groups, phosphine groups, phosphonium groups, nitrile groups, mercapto groups, nitroso groups, halogen atoms, nitro groups, sulfone groups, acyl groups, cyanopropyl groups, allyl groups, mixtures thereof, and the like, wherein two or more substituents can be joined together to form a ring, n is an integer representing the number of repeat —OSi(R₇)(R₈)— monomer units, typically being from about 3 to about 100, preferably from about 3 to about 50, and more preferably from about 3 to about 20, although the value of n can be outside of these ranges, a is an integer representing the number of repeat —OSi(R₁₀)(R₁₂-lightfastness moiety)— monomer units, typically being from 1 to about 20, preferably from 1 to about 10, and more preferably from 1 to about 5, although the value of a can be outside of these ranges, and c is an integer representing the number of repeat —OSi(R₉)(R₁₁-hydrophilic segment)— monomer units, typically being from 1 to about 50, preferably from 1 to about 20, and more preferably from 1 to about 10, although the value of c can be outside of these ranges. The number average molecular weight of the polymer typically is from about 1,000 to about 50,000, and preferably from about 2,000 to about 20,000, although the value can be outside of these ranges.

Example of suitable lightfastness moieties include 2-(3-(2H-benzotriazol-2-yl)-4-hydroxyphenyl) groups, of the formulae

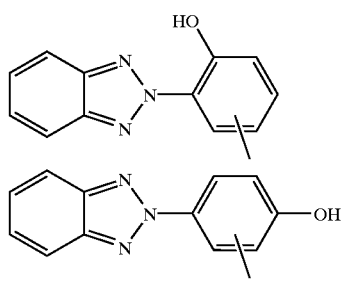

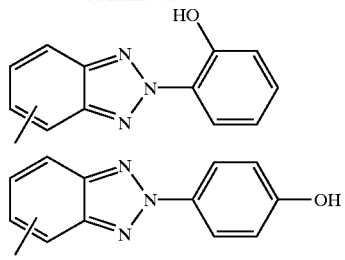

hydroxybenzophenone groups, of the formulae

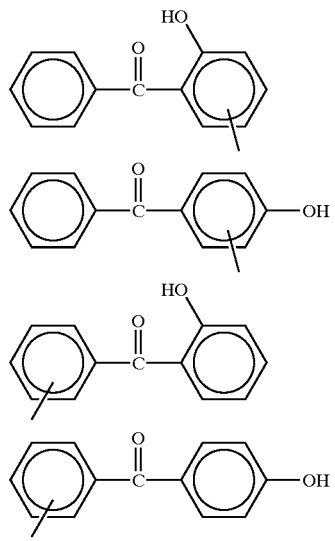

hydroxybenzoic acid groups, of the formula

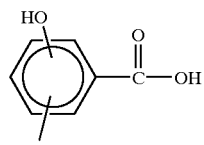

alkoxybenzoic acid groups, of the formula

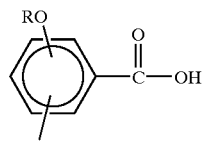

wherein R is an alkyl group (including linear, branched, saturated, unsaturated, cyclic, and substituted alkyl groups, and wherein hetero atoms, such as oxygen, sulfur, nitrogen, silicon, phosphorus, or the like, can be placed between the carbon atoms in the alkyl group), typically with from 1 to about 22 carbon atoms, preferably with from 1 to about 12 carbon atoms, and more preferably with from 1 to about 6 carbon atoms, although the number of carbon atoms can be outside of these ranges, an aryl group (including substituted aryl groups), typically with from about 6 to about 24 carbon atoms, preferably with from about 6 to about 12 carbon atoms, and more preferably with from about 6 to about 10 carbon atoms, although the number of carbon atoms can be outside of these ranges, an arylalkyl group (including substituted arylalkyl groups), typically with from about 7 to about 25 carbon atoms, preferably with from about 7 to about 13 carbon atoms, and more preferably with from about 7 to about 11 carbon atoms, although the number of carbon atoms can be outside of these ranges, an alkylaryl group (including substituted alkylaryl groups), typically with from about 7 to about 25 carbon atoms, preferably with from about 7 to about 13 carbon atoms, and more preferably with from about 7 to about 11 carbon atoms, although the number of carbon atoms can be outside of these ranges, wherein the substituents on the substituted alkyl, aryl, arylalkyl, and alkylaryl groups can be (but are not limited to) hydroxy groups, amine groups, ammonium groups, cyano groups, pyridine groups, pyridinium groups, ether groups, aldehyde groups, ketone groups, ester groups, amide groups, carbonyl groups, sulfide groups, sulfoxide groups, phosphine groups, phosphonium groups, nitrile groups, mercapto groups, nitroso groups, halogen atoms, nitro groups, sulfone groups, acyl groups, cyanopropyl groups, allyl groups, mixtures thereof, and the like, wherein two or more substituents can be joined together to form a ring, esters of substituted benzoic acids, including those of the formula

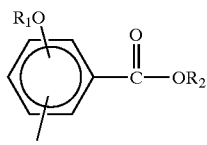

wherein $R_1$ and $R_2$ each, independently of the other, is an alkyl group (including linear, branched, saturated, unsaturated, cyclic, and substituted alkyl groups, and wherein hetero atoms, such as oxygen, sulfur, nitrogen, silicon, phosphorus, or the like, can be placed between the carbon atoms in the alkyl group), typically with from 1 to about 22 carbon atoms, preferably with from 1 to about 12 carbon atoms, and more preferably with from 1 to about 6 carbon atoms, although the number of carbon atoms can be outside of these ranges, an aryl group (including substituted aryl groups), typically with from about 6 to about 24 carbon atoms, preferably with from about 6 to about 12 carbon atoms, and more preferably with from about 6 to about 10 carbon atoms, although the number of carbon atoms can be outside of these ranges, an arylalkyl group (including substituted arylalkyl groups), typically with from about 7 to about 25 carbon atoms, preferably with from about 7 to about 13 carbon atoms, and more preferably with from about 7 to about 11 carbon atoms, although the number of carbon atoms can be outside of these ranges, an alkylaryl group (including substituted alkylaryl groups), typically with from about 7 to about 25 carbon atoms, preferably with from about 7 to about 13 carbon atoms, and more preferably with from about 7 to about 11 carbon atoms, although the number of carbon atoms can be outside of these ranges, wherein the substituents on the substituted alkyl, aryl, arylalkyl, and alkylaryl groups can be (but are not limited to) hydroxy groups, amine groups, ammonium groups, cyano groups, pyridine groups, pyridinium groups, ether groups, aldehyde groups, ketone groups, ester groups, amide groups, carbonyl groups, sulfide groups, sulfoxide groups, phosphine groups, phosphonium groups, nitrile groups, mercapto groups, nitroso groups, halogen atoms, nitro groups, sulfone groups, acyl groups, cyanopropyl groups, allyl groups, mixtures thereof, and the like, wherein two or more substituents can be joined together to form a ring, (hydroxyphenyl)-1,3,5-triazine groups, of the formulae

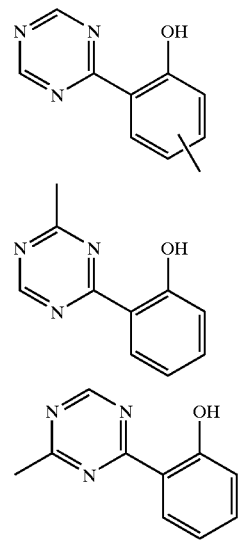

phenylbenzimidazole sulfonic acid groups, of the formulae

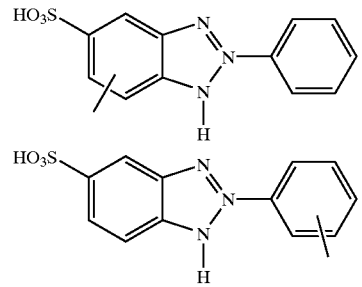

reducing sugar groups, such as raffinose, those of the formula

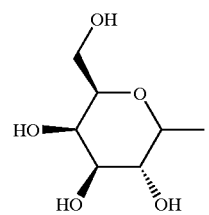

other reducing sugars, and the like.

Examples of suitable anionic lightfastness moieties include (hydroxyphenyl)-benzotriazoles, of the general formulae

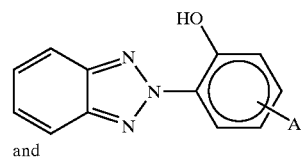

and

-continued

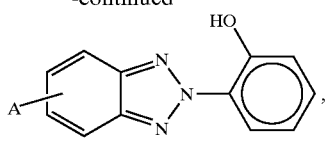

hydroxybenzophenones, of the general formulae

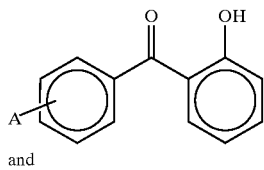

and

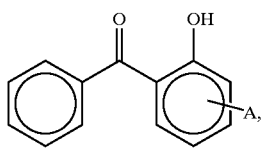

hydroxybenzoic acids, of the general formulae

and

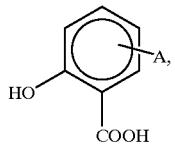

alkoxybenzoic acids, of the general formulae

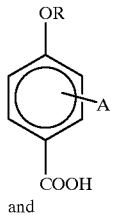

and

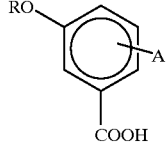

and

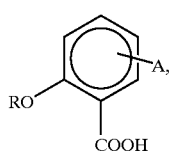

wherein R is an alkyl group, typically with from 1 to about 12 carbon atoms, although the number of carbon atoms can be outside of this range, esters of substituted benzoic acids, of the general formula

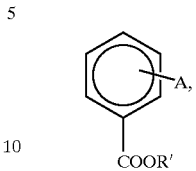

wherein R' is an alkyl group, typically with from 1 to about 12 carbon atoms, although the number of carbon atoms can be outside of this range, (hydroxyphenyl)-1,3,5 triazines, of the general formulae

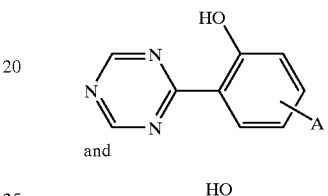

and

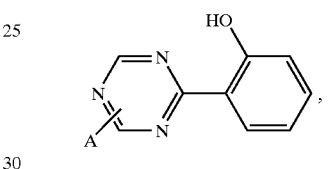

and the like, wherein in all of the above generic formulae, A is a substituent containing an anionic moiety. A can be either an anionic moiety by itself, such as a carboxylate group, sulfonate group, phosphonate group, or the like, or can be an aliphatic or aromatic group (including aliphatic and aromatic groups containing hetero atoms, such as oxygen, nitrogen, sulfur, silicon, phosphorus, or the like) to which an anionic group is attached. It is to be understood that other substituents can also be present on materials of these formulae. Many compounds in these classes and having ionizable ionic substituents are commercially available, such as 2-hydroxy-4-methoxybenzophenone-5-sulfonic acid; 2,2'-dihydroxy-4,4'-dimethoxybenzophenone-5-sulfonic acid; 2,3-dimethoxybenzoic acid; 3,4-dimethoxybenzoic acid; 3,5-dimethoxybenzoic acid; 2,5-dimethoxybenzoic acid; 2,6-dimethoxybenzoic acid 3,4-dimethoxybenzenesulfonic acid; 3,4,5-trimethoxybenzoic acid, 2,4,5-trimethoxybenzoic acid; 4,5-dimethoxyphthalic acid; 2,3-bis-isopropylidenedioxybenzoic acid; 2,3-bis-(carboxymethyloxy)-benzoic acid; 2,5-dihydroxyphenylacetic acid; and the like, commercially available from sources such as Aldrich Chemical Co., Milwaukee, Wis., and Chem Service Inc., Westchester, Pa. Also suitable are compounds and salts thereof such as those of the following formulae, disclosed in, for example, U.S. Pat. No. 5,686,633, the disclosure of which is totally incorporated herein by reference:

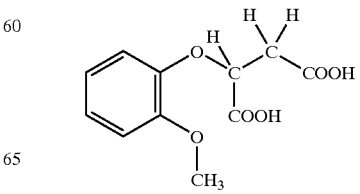

-continued
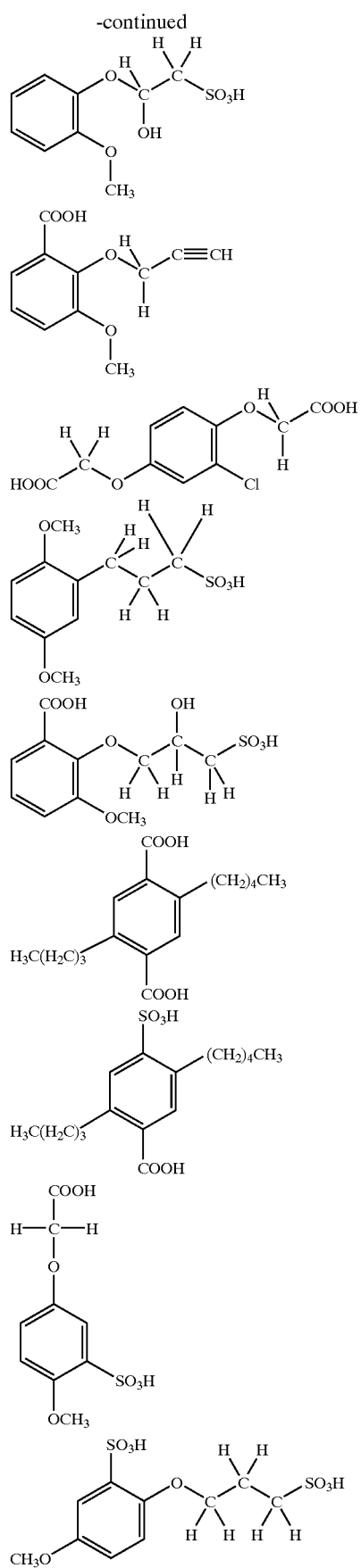
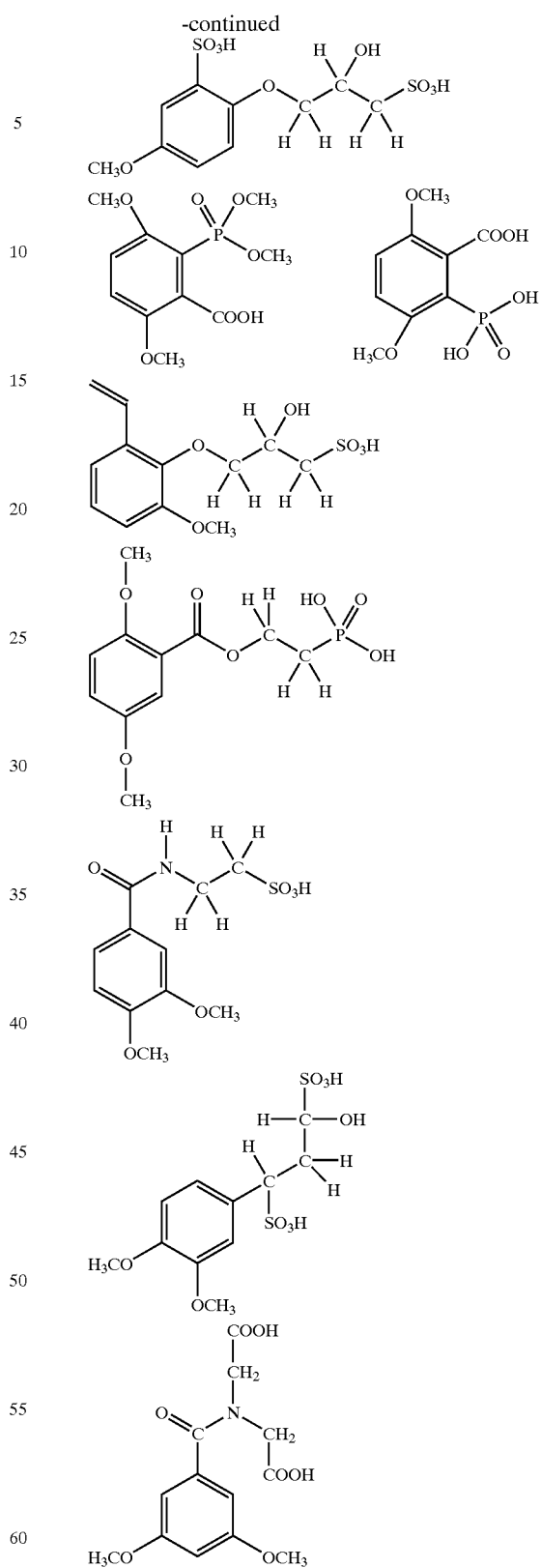
and the like, as well as mixtures thereof. Materials of these formulae can be prepared as disclosed in, for example, U.S. Pat. No. 5,686,633, the disclosure of which is totally incorporated herein by reference.

Examples of suitable cationic lightfastness moieties include (but are not limited to) 2-(3-(2H-benzotriazol-2-yl)-4-hydroxyphenyl) quaternary compounds, of the general formulae

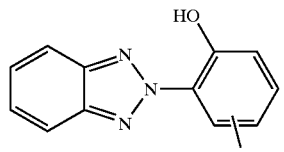

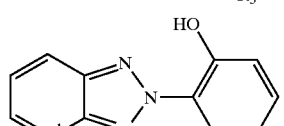

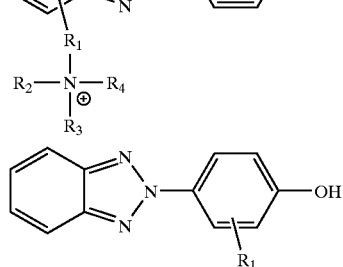

or

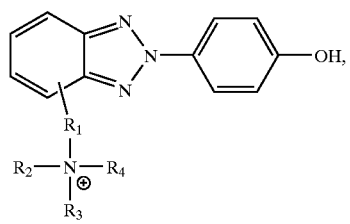

hydroxybenzophenone quaternary compounds, of the general formulae

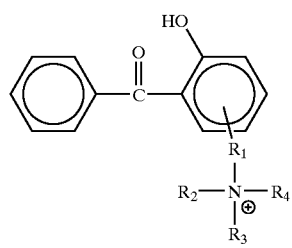

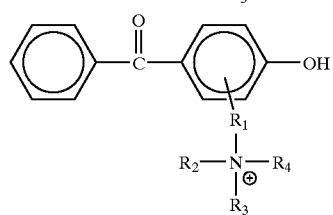

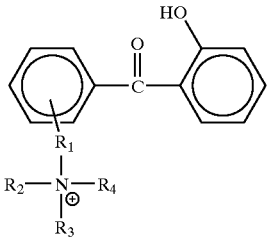

or

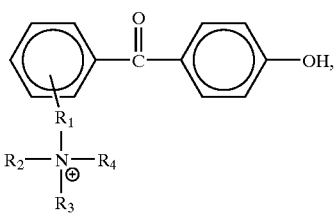

quaternary ammonium derivatives of dialkylaminobenzoates, of the general formula

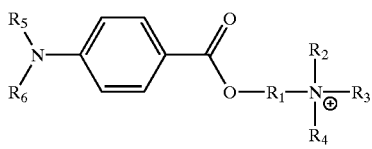

wherein $R_5$ and $R_6$ each, independently of the other, is an alkyl group, typically with from 1 to about 6 carbon atoms, although the number of carbon atoms can be outside of this range, or an arylalkyl group, typically with from about 7 to about 12 carbon atoms, such as a benzyl group, although the number of carbon atoms can be outside of this range, and the like, wherein $R_1$ is an alkylene group (including linear, branched, saturated, cyclic, and substituted alkylene groups, and wherein hetero atoms, such as oxygen, sulfur, nitrogen, silicon, phosphorus, or the like, can be placed between the carbon atoms in the alkylene group), typically with from 1 to about 10 carbon atoms, and preferably with from 1 to about 4 carbon atoms, although the number of carbon atoms can be outside of this range, an arylalkylene group (including substituted arylalkylene groups), typically with from 7 to about 20 carbon atoms, more preferably with from 7 to about 13 carbon atoms, although the number of carbon atoms can be outside of this range, or a polyalkyleneoxy group (including substituted polyalkyleneoxy groups), typically polyethyleneoxy groups or polypropyleneoxy groups, typically with from 2 to about 22 repeat alkyleneoxy units, and preferably with from 2 to about 10 repeat alkyleneoxy units, although the number of repeat alkyleneoxy units can be outside of these ranges, and $R_2$, $R_3$, and $R_4$ each, independently of the others, is a hydrogen atom, an alkyl group (including linear, branched, saturated, unsaturated, cyclic, and substituted alkyl groups, and wherein hetero atoms, such as oxygen, sulfur, nitrogen, silicon, phosphorus, or the like, can be placed between the carbon atoms in the alkyl group), typically with from 1 to about 10 carbon atoms, and preferably with from 1 to about 4 carbon atoms, although the number of carbon atoms can be outside of this range, an aryl group (including substituted aryl groups), typically with from 6 to about 18 carbon atoms, more preferably with from 6 to about 12 carbon atoms, although the number of carbon atoms can be outside of this range, an arylalkyl group (including substituted arylalkyl groups), typically with from 7 to about 20 carbon atoms, more preferably with from 7 to about 13 carbon atoms, although the number of carbon atoms can be outside of this range, an alkylaryl group (including substituted alkylaryl groups), typically with from 7 to about 20 carbon atoms, more preferably with from 7 to about 13 carbon atoms, although the number of carbon atoms can be outside of this range, an alkoxy group (including substituted alkoxy groups), typically with from 1 to about 10 carbon atoms, and preferably with from 1 to about 4 carbon atoms, although the number of carbon atoms can be outside of this range, or a polyalkyleneoxy group (including substituted polyalkyleneoxy groups), typically polyethyleneoxy groups or polypropyleneoxy groups, typically with from 2 to about 22 repeat alkyleneoxy units, and preferably with from 2 to about 10 repeat alkyleneoxy units, although the number of repeat alkyleneoxy units can be outside of these ranges, wherein the substituents on the substituted alkyl, alkylene, aryl, arylene, arylalkyl, arylalkylene, alkylaryl, alkylarylene, alkoxy, alkyleneoxy, and polyalkyleneoxy groups can be (but are not limited to) halogen atoms, amine groups, imine groups, ammonium groups, cyano groups, pyridine groups, pyridinium groups, ether groups, aldehyde groups, ketone groups, ester groups, amide groups, carbonyl groups, thiocarbonyl groups, sulfate groups, sulfonate groups, sulfide groups, sulfoxide groups, phosphine groups, phosphonium groups, phosphate groups, nitrile groups, mercapto groups, nitro groups, nitroso groups, sulfone groups, acyl groups, acid anhydride groups, azide groups, mixtures thereof, and the like, as well as mixtures thereof, and wherein two or more substituents can be joined together to form a ring.

The 2-(3-(2H-benzotriazol-2-yl)-4-hydroxyphenyl) quaternary compounds can be prepared by any desired or suitable method. For example, N-2-(3-(benzotriazole-2-yl)-4-hydroxyphenyl proplonyl amino) ethyl-N,N,N-trimethyl ammonium chloride can be made by the synthetic process outlined below:

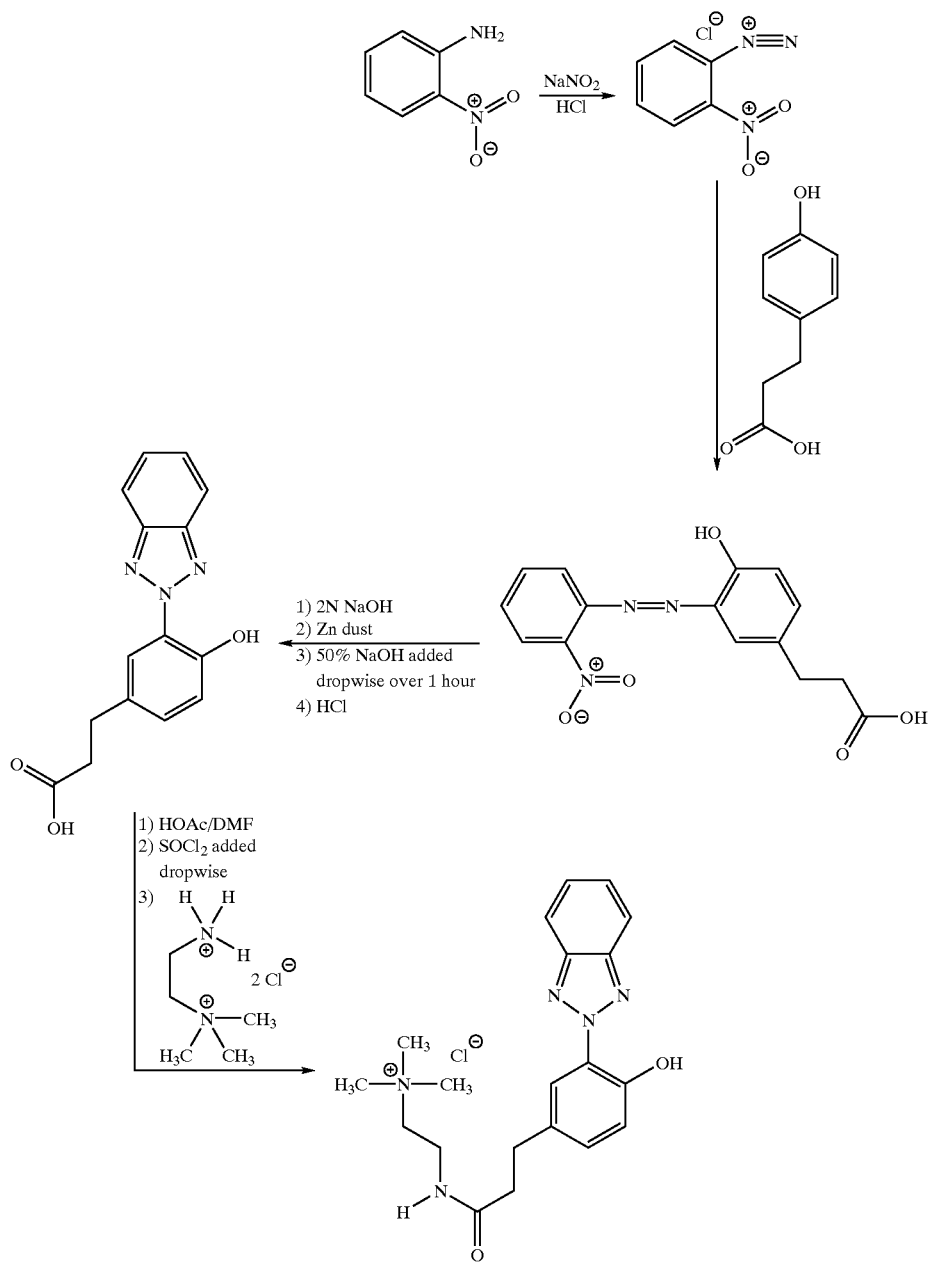

2-Nitroaniline is reacted with sodium nitrite in hydrochloric acid to yield the diazonium salt. The diazonium salt is reacted stoichiometrically with 2-(4-hydroxyphenyl) propionic acid to yield the corresponding azo compound. Dissolution in 2N NaOH and addition of Zn dust, followed by dropwise addition of 50 percent NaOH over a period of about one hour to a reaction mixture held at 45° C. yields the desired 2-hydroxyphenybenzotriazole. 2-(3-(2H-benzotriazol-2-yl)-4-hydroxyphenyl)propionic acid is isolated by acidification with hydrochloric acid and isolation of the crystalline precipitated product is by filtration. 2-(3-(2H-benzotriazol-2-yl)-4-hydroxyphenyl)propionyl aminoethyl-trimethylammonium chloride is obtained by stoichiometric reaction of a solution of 2-(3-(2H-benzotriazol-2-yl)-4-hydroxyphenyl)propionic acid in a mixture of acetic acid and dimethylformamide, with thionyl chloride, added dropwise, to generate 2-(3-(2H-benzotriazol-2-yl)-4-hydroxyphenyl)propionyl chloride. The acid chloride is reacted in situ with 2-aminoethyl(trimethylammonium chloride hydrochloride to yield 2-(3-(2H-benzotriazol-2-yl)-4-hydroxyphenyl)propionyl aminoethyl-trimethylammonium chloride, which is isolated by dilution with water and filtration. In all of the reactions in this sequence the retain mixture is cooled in a water bath to hold the reaction temperature at about 25° C.

The quaternary dimethylaminobenzoic acid derivative

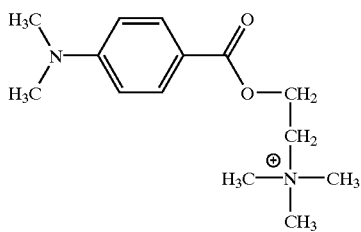

can be synthesized by the reaction of dimethylaminobenzoic acid with choline chloride in the presence of thionyl chloride.

The hydrophilic moiety can be a separate substituent, as in Formulae I, II, and III, or integral to (having) an anionic substituent the counterion of which is a cationic lightfastness moiety, as in Formula IV, or integral to (having) a cationic substituent the counterion of which is an anionic lightfastness moiety, as in Formula V. Examples of suitable hydrophilic moieties include polyoxyalkylene chains, such as polyethylene oxide, polypropylene oxide, polybutylene oxide, random or block copolymers of two or more oxyalkylene monomers, or the like, such as those of the general formulae

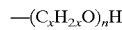

and

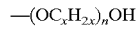

wherein x, independently in each single repeat alkylene oxide unit, is an integer of 2, 3, or 4 and n is an integer representing the number of repeat alkylene oxide units, and is typically from 1 to about 60, preferably from 1 to about 30, and more preferably from 1 to about 10, although the value of n can be outside of these ranges, poly(2-alkyloxazoline)s, such as those of the general formula

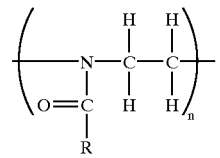

wherein R is an alkyl group, including linear, branched, cyclic, and unsaturated alkyl groups, typically with from 1 to about 22 carbons and preferably with from 1 to about 6 carbon atoms, although the number of carbon atoms can be outside of these ranges, an aryl group, typically with from 6 to about 12 carbon atoms, with 6 carbon atoms being preferred, although the number of carbon atoms can be outside of this range, an arylalkyl group, typically with from 7 to about 28 carbon atoms, and preferably with from 7 to about 10 carbon atoms, although the number of carbon atoms can be outside of these ranges, or an alkylaryl group, typically with from 7 to about 28 carbon atoms, and preferably with from 7 to about 10 carbon atoms, although the number of carbon atoms can be outside of these ranges, and n is an integer representing the number of repeat monomer units, and is typically from 1 to about 100, preferably from 1 to about 50, and more preferably from 1 to about 30, although the value of n can be outside of these ranges, poly(ethyleneimine) chains, including those of the general formula

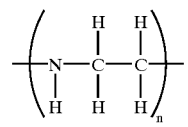

wherein n is an integer representing the number of repeat monomer units, and is typically from 1 to about 100, preferably from 1 to about 50, and more preferably from 1 to about 30, although the value of n can be outside of these ranges, or the like.

Commercially available materials include those of the general formula

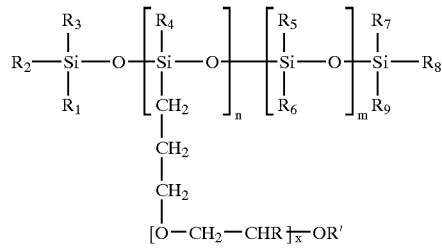

wherein R and R' each, independently of the other, is hydrogen or methyl, and $R_1$, $R_2$, $R_3$, $R_4$, $R_5$, $R_6$, $R_7$, $R_8$, and $R_9$ each, independently of the others, is an alkyl group, including linear, branched, cyclic, and unsaturated alkyl groups, typically with from 1 to about 22 carbons and preferably with from 1 to about 5 carbon atoms, although the number of carbon atoms can be outside of these ranges, an aryl group, typically with from 6 to about 12 carbon atoms, with 6 carbon atoms being preferred, although the number of carbon atoms can be outside of this range, or an arylalkyl group (with either the alkyl or the aryl portion of the group being attached to the silicon atom), typically with from 7 to about 28 carbon atoms, and preferably with from 7 to about 10 carbon atoms, although the number of carbon atoms can be outside of these ranges, and wherein the alkyl, aryl, or arylalkyl groups can, if desired, be substituted with substituents that do not significantly impair the ability of the polymer to form a uniform monolayer on a paper surface, such as cyanopropyl groups, halide groups, or the like, although substituents are not preferred, and m, n, and x are each integers representing the number of repeat monomer units, x typically being an integer of from about 6 to about 30, and preferably from about 9 to about 20, although the value can be outside of these ranges. The relative molar ratio of n and m typically falls within the range of from about 3:97 to about 60:40, although the relative ratio can be outside of this range. Molecular weights of preferred materials typically are from about 600 to about 30,000 grams per mole, although the molecular weight can be outside of this range. Commercially available examples of this class of materials are the TEGOPREN®s, available from Goldschmidt Chemical, Hopewell, Va., such as TEGOPREN® 5842, wherein x is 16 and the mole ratio of n to m is about 22:78; the DBE series of hydrophilic silicones available form Gelest, Inc., Tullytown, Pa., the SILWET® silicone surfactant series available from Witco Corporation, OrganoSilicones Group, Greenwich, Conn.; Silicone Polyol copolymers available from Genesee Polymers Corporation, Flint, Mich.; and the like. Siloxane-oxyethylene block and graft copolymers typically are prepared by hydrosilylation of monoallyl or monovinyl ethers of polyethylene oxide glycols under the catalytic action of chloroplatinic acid by (Si—H) groups in dimethylsiloxane/methylhydrosiloxane copolymers, as disclosed in, for example, U.S. Pat. No. 2,486,458, the disclosure of which is totally incorporated herein by reference. The controlled synthesis of AB, ABA, and $(AB)_n$ type polyethylene oxide (A) and polydialkylsiloxane (B) copolymers by hydrosilylation of mono- or diallyl-terminated polyethylene oxide oligomers and telechelic (Si—H) terminated polydialkylsiloxane oligomers is also disclosed by, for example, Haessilin, *Makromol. Chem.*, 186, p. 357 (1985), the disclosure of which is totally incorporated herein by reference. Further information regarding the synthesis of such block and graft copolymers is also disclosed in, for example, U.S. Pat. No. 2,846,548, British Patent 983,850; British Patent 955,916; B. Kanner, B. Prokai, C. S. Eschbach, and G. J. Murphy, *J. Cellular Plast.*, November/December 315 (1979); H. W. Haesslin, H. F. Eicke and G. Riess, *Makromol. Chem.*, 185, 2625 (1984); M. Galin, A. Mathis, *Macromolecules*, 14, 677 (1981); and I. Yilgör and J. E. McGrath, "Polysiloxane-Containing Copolymers: A survey of Recent Developments," *Advances in Polymer Science*, Volume 86, pp. 1–86 (Springer-Verlag 1988), the disclosures of each of which are totally incorporated herein by reference.

Commercially available materials also include those of the general formula

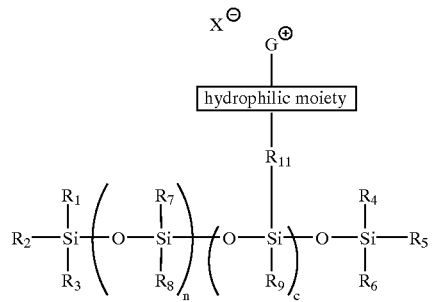

wherein $R_1$, $R_2$, $R_3$, $R_4$, $R_5$, $R_6$, $R_7$, $R_8$, and $R_9$ each, independently of the others, is an alkyl group, including linear, branched, cyclic, and unsaturated alkyl groups, typically with from 1 to about 22 carbons and preferably with from 1 to about 5 carbon atoms, although the number of carbon atoms can be outside of these ranges, an aryl group, typically with from 6 to about 12 carbon atoms, with 6 carbon atoms being preferred, although the number of carbon atoms can be outside of this range, or an arylalkyl group (with either the alkyl or the aryl portion of the group being attached to the silicon atom), typically with from 7 to about 28 carbon atoms, and preferably with from 7 to about 10 carbon atoms, although the number of carbon atoms can be outside of these ranges, and wherein the alkyl, aryl, or arylalkyl groups can, if desired, be substituted with substituents that do not significantly impair the ability of the polymer to form a uniform monolayer on a paper surface, such as cyanopropyl groups, halide groups, or the like, although substituents are not preferred, $R_{11}$ is a spacer group which is either an alkylene group, typically with from 2 to about 12 carbon atoms, and preferably with from 2 to about 6 carbon atoms, or an arylalkylene group wherein the alkyl portion is attached to the silicon atom and the aryl portion is attached to the G group, with the alkyl portion of the arylalkylene group typically having from 2 to about 12 carbon atoms, and preferably having from 2 to about 6 carbon atoms, and with the aryl portion of the arylalkylene group typically having 6 carbon atoms, n and c are each integers representing the number of repeat monomer units, G is a cationic functional group capable of binding anionic lightfastness agents as defined hereinabove, and X is an anion, including (but not limited to) halides, such as chloride, bromide, and iodide, nitrate, sulfate, sulfite, or the like. In a preferred embodiment, the R groups are all methyl groups. These polymers can be block copolymers, random copolymers, or alternating copolymers. Typically, the "n" monomers are present in the polymer in an amount of from 0 to about 99 mole percent, and preferably from about 50 to about 95 mole percent, and the "c" monomers are typically present in the polymer in an amount of from about 1 to 100 mole percent, and preferably from about 5 to about 50 mole percent, although the relative ratio of monomers can be outside of these ranges. The number average molecular weight of these polymers typically is from about 500 to about 30,000, and preferably from about 1,000 to about 5,000, although the value can be outside of these ranges. One specific example of a member of this class of organopolysiloxane copolymers is that of quaternary amino functionalized siloxane polymers, including those of the general formula

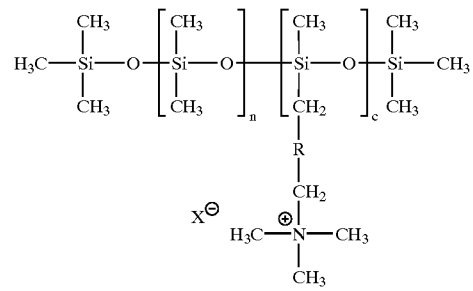

wherein n and c are each integers representing the number of repeat monomer units, X is an anion, and R is a methylene group or a benzyl group. A commercially available example of this class of materials is QMS-435, a hydrophilic silicone supplied by Gelest, Inc., Tullytown, Pa.

Polysiloxanes of the present invention can be prepared by any desired or effective method. For example, a commercially available polymer or oligomer of the general formula

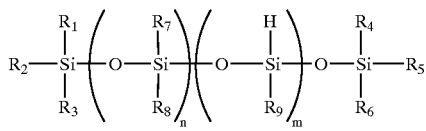

can be reacted with a lightfastness compound having a terminal >C=C< group and an alkoxy or polyalkyleneoxy compound having a terminal >C=C< group in the presence of a platinum catalyst. Siloxane-oxyethylene block and graft copolymers typically are prepared by hydrosilylation of monoallyl or monovinyl ethers of polyethylene oxide glycols under the catalytic action of chloroplatinic acid by (Si—H) groups in dimethylsiloxane/methylhydrosiloxane copolymers, as disclosed in, for example, U.S. Pat. No. 2,486,458, the disclosure of which is totally incorporated herein by reference. The controlled synthesis of AB, ABA, and (AB)$_n$ type polyethylene oxide (A) and polydialkylsiloxane (B) copolymers by hydrosilylation of mono- or diallyl-terminated polyethylene oxide oligomers and telechelic (Si—H) terminated polydialkylsiloxane oligomers is also disclosed by, for example, Haessilin, *Makromol. Chem.*, 186, p. 357 (1985), the disclosure of which is totally incorporated herein by reference. Further information regarding the synthesis of such block and graft copolymers is also disclosed in, for example, U.S. Pat. No. 2,846,548; British Patent 983,850; British Patent 955,916; B. Kanner, B. Prokai, C. S. Eschbach, and G. J. Murphy, *J. Cellular Plast.*, November/December 315 (1979); H. W. Haesslin, H. F. Eicke and G. Riess, *Makromol. Chem.*, 185, 2625 (1984); M. Galin, A. Mathis, *Macromolecules*, 14, 677 (1981); and I. Yilgor and J. E. McGrath, "Polysiloxane-Containing Copolymers: A survey of Recent Developments," *Advances in Polymer Science*, Volume 86, pp. 1–86 (Springer-Verlag 1988), the disclosures of each of which are totally incorporated herein by reference. Siloxane-oxyethylene block and graft copolymers with covalently bound lightfastness substituents can be prepared by hydrosilylation of vinyl or allyl derivatives of lightfastness moieties prior to or simultaneously with the hydrosilylation of monoallyl or monovinyl ethers of polyethylene oxide glycols under the catalytic action of chloroplatinic acid by (Si—H) groups in dimethylsiloxane/methylhydrosiloxane copolymers.

An illustrative example of such a reaction is as follows:

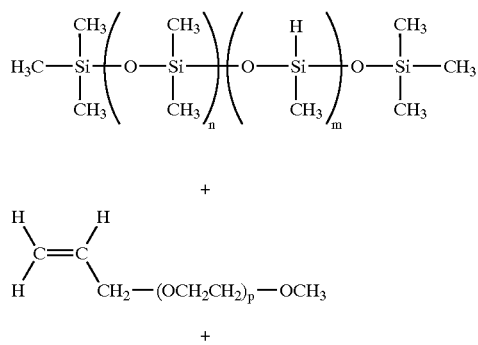

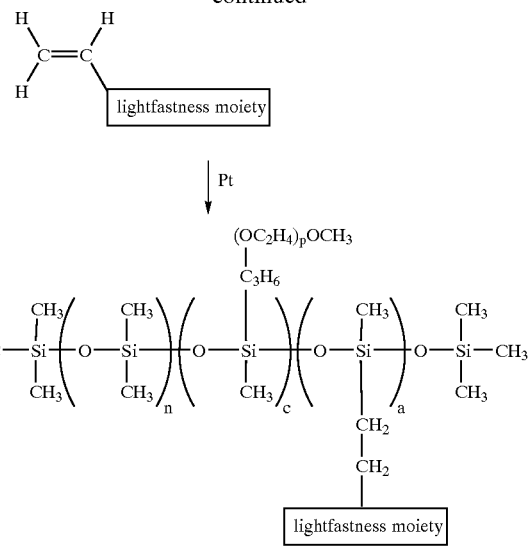

wherein m = a + c and [lightfastness moiety] is, for example,

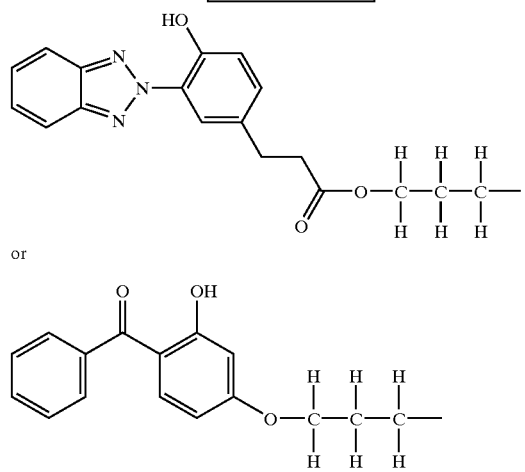

4-alloxy-2-hydroxy benzophenone is commercially available (Aldrich 41,583-9) as are 2-(3-2H-benzotriazol-2-yl)-4-hydroxyphenyl)ethyl methacrylate (Aldrich 41,343-7) eugenol (Aldrich E5,179-1), 4-allyl-1,2-dimethoxybenzene (Aldrich 28,442-4), and 4-allyl-2,6-dimethoxyphenol (Aldrich A3160-1). 2-(3-2H-benzotriazol-2-yl)-4-hydroxyphenyl)ethylpentenoate can be synthesized by esterification of 2-(3-2H-benzotriazol-2-yl)-4-hydroxyphenethyl alcohol (Aldrich 43,071-4) with pentenoic acid (Aldrich 24,592-5) or pentenoic anhydride (Aldrich 47,180-1).

In addition, a commercially available polymer or oligomer of the general formula

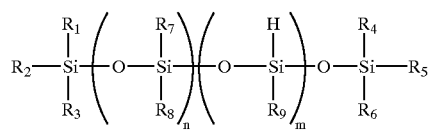

can be reacted with an anionic compound having a terminal >C=C< group and an alkoxy or polyalkyleneoxy compound having a terminal >C=C< group in the presence of a platinum catalyst. An illustrative example of such a reaction is as follows:

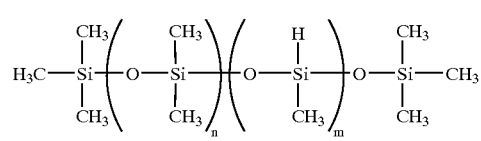

+

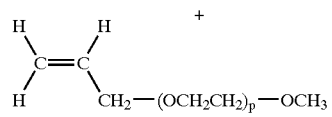

+

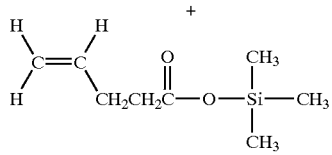

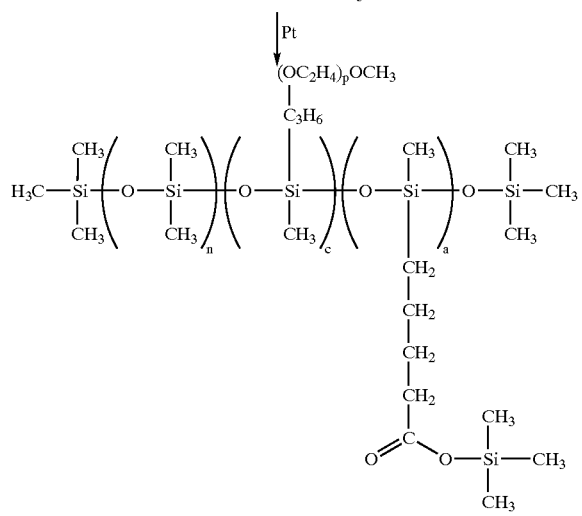

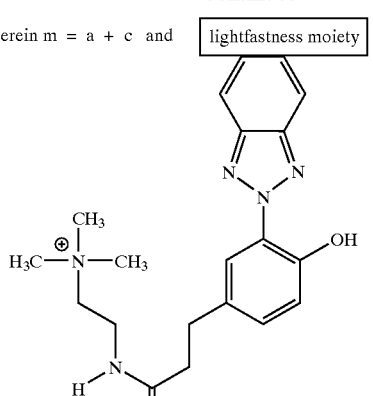

or

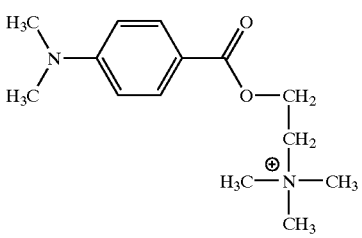

wherein m = a + c and ⊕lightfastness moiety⊕ is, for example,

In aqueous solutions with a pH greater than about 5, the trimethylsilyl ester group is ionized to carboxylate, —COO⁻. Introduction of a lightfastness moiety bearing a cationic substituent results in ion exchange to associate the lightfastness moiety with a anionic group covalently attached to the backbone of the hydrophilic siloxane, illustrated as follows:

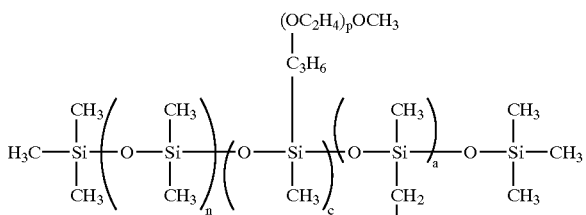
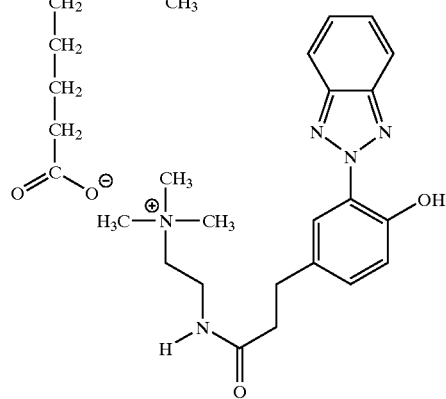

The quaternary ammonium substituted hydroxyphenyl benzotriazole illustrated above can be synthesized by the synthetic process outlined below:

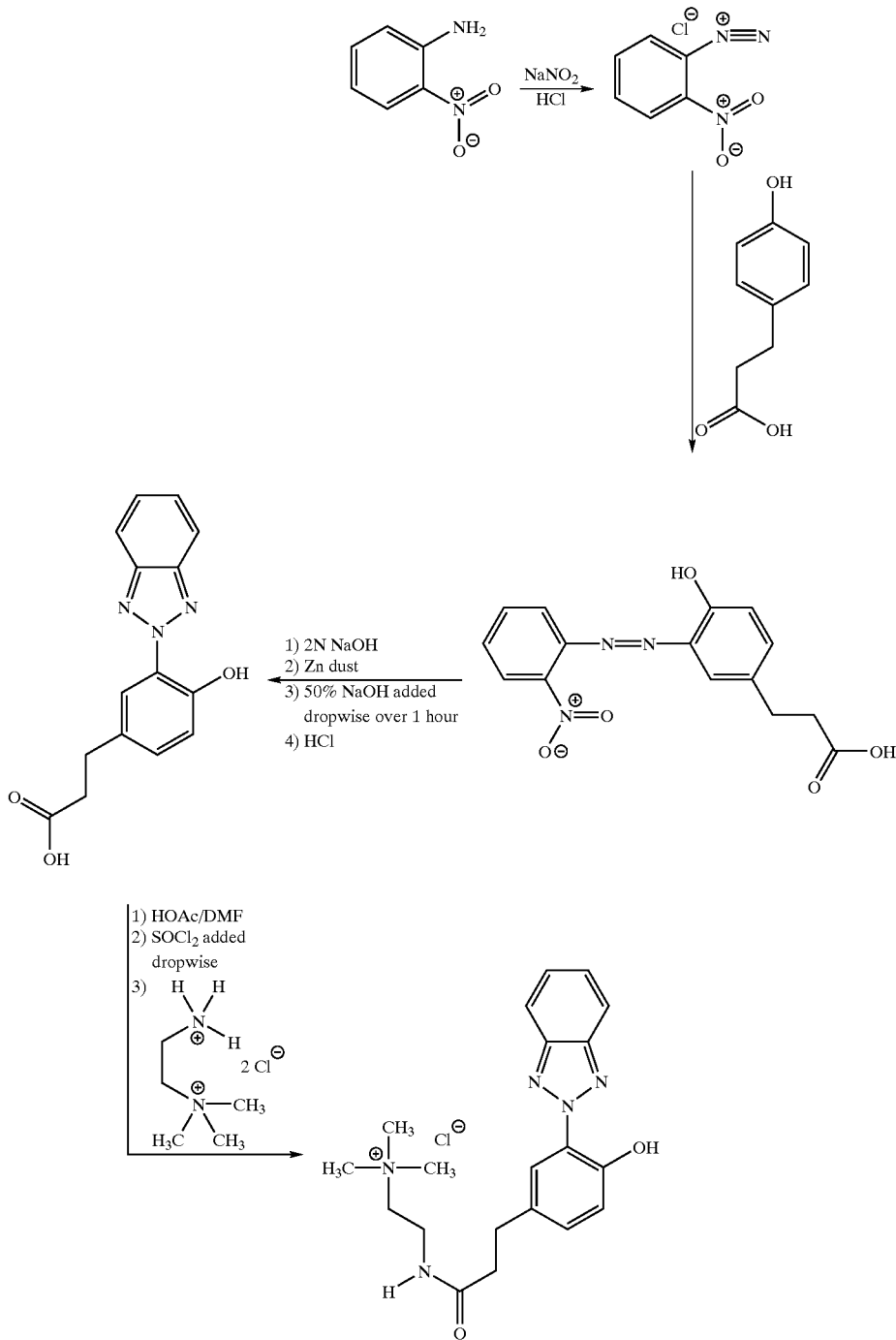

2-Nitroaniline is reacted with sodium nitrite in hydrochloric acid to yield the diazonium salt. The diazonium salt is reacted stoichiometrically with 2-(4-hydroxyphenyl) propionic acid to yield the corresponding azo compound. Dissolution in 2N NaOH and addition of Zn dust, followed by dropwise addition of 50 percent NaOH over a period of about one hour to a reaction mixture held at 45° C. yields the desired 2-hydroxyphenybenzotriazole. 2-(3-(2H-benzotriazol-2-yl)-4-hydroxyphenyl)propionic acid is isolated by acidification with hydrochloric acid and isolation of the crystalline precipitated product is by filtration. 2-(3-(2H-benzotriazol-2-yl)-4-hydroxyphenyl)propionyl aminoethyl-trimethylammonium chloride is obtained by stoichiometric reaction of a solution of 2-(3-(2H-benzotriazol-2-yl)-4-hydroxyphenyl)propionic acid in a mixture of acetic acid and dimethylformamide, with thionyl chloride, added dropwise, to generate 2-(3-(2H-benzotriazol-2-yl)-4-hydroxyphenyl)propionyl chloride. The acid chloride is reacted in situ with 2-aminoethyl(trimethylammonium chloride hydrochloride to yield 2-(3-(2H-benzotriazol-2-yl)-4-hydroxyphenyl)propionyl aminoethyl-trimethylammonium chloride, which is isolated by dilution with water and filtration. In all of the reactions in this sequence the retain mixture is cooled in a water bath to hold the reaction temperature at about 25° C.

The quaternary dimethylaminobenzoic acid derivative

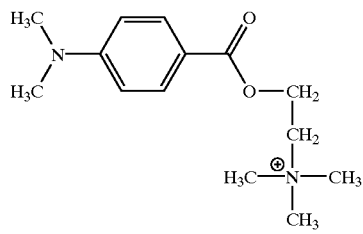

can be synthesized by the reaction of dimethylaminobenzoic acid with choline chloride in the presence of thionyl chloride.

Further, commercially available cationic substituted polysiloxane oligomers or polymers can be subjected to an ionic exchange process to associate the cationic groups thereon with a lightfastness compound substituted with an anionic moiety. The ion exchange can be performed by simple mixing of a solution containing the anionic lightfastness agent in a solvent such as acetone with a solution containing the cationic polysiloxane in a solvent such as acetone. An illustrative example of such a reaction is as follows:

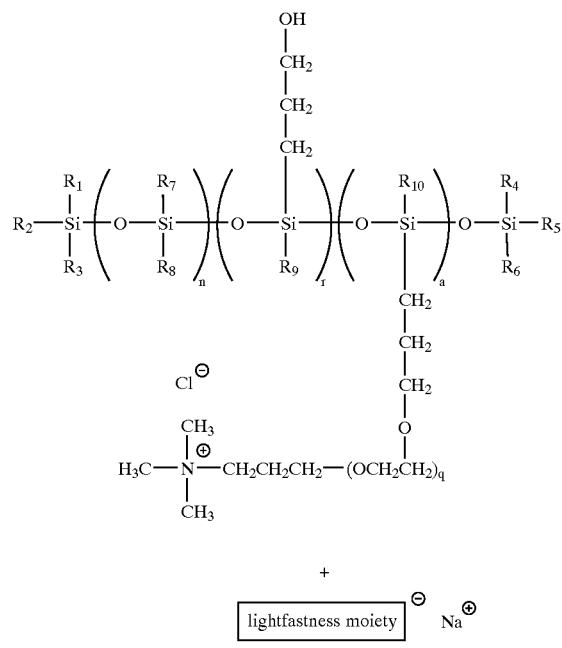

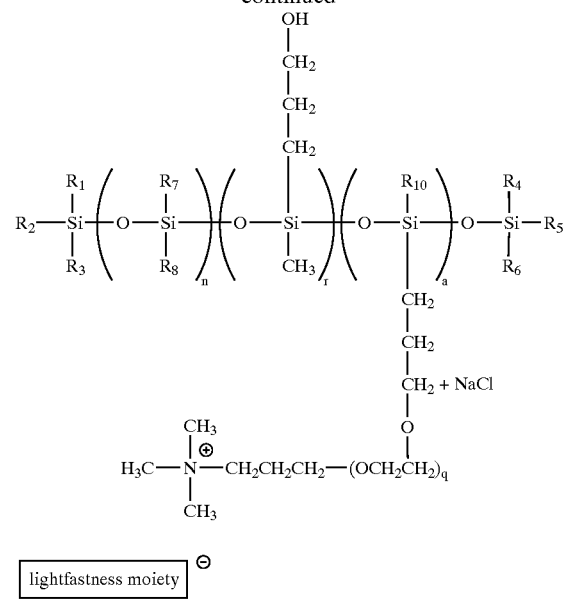

wherein r is an integer representing the number of repeat —OSi($R_9$)($C_3H_5$OH)— monomer units, typically from about 3 to about 30, and preferably from about 3 to about 10 although the value of r can be outside of these ranges, q is an integer representing the number of repeat —OCH$_2$CH$_2$— monomer units, typically from about 6 to about 30, and preferably from about 6 to about 10, although the value of q can be outside of these ranges, and

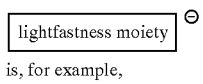

is, for example,

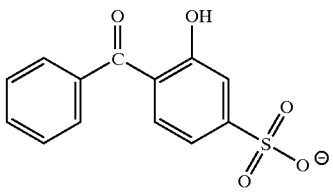

Sulfonate substituted lightfastness moieties can be obtained from a variety of commercial sources, such as Chem Service Inc., Westchester, Pa., and Lancaster Synthesis Inc., Windham, N.J. Polymeric and oligomeric siloxanes having quaternary ammonium substituents thereon are commercially available as, for example, TEGOPREN® 6922 and TEGOPREN® 6920, obtainable from Goldschmidt Chemical, Hopewell, Va., QMS435, available from Gelest, Inc., Tullytown, Pa., and poly(dimethylsiloxane-co-methyl (3-hydroxypropyl)siloxane-graft-poly(ethylene glycol)(3-(trimethylammonio)propyl chloride)ether), available from Aldrich Chemical Co., Milwaukee, Wis.

A similar process can be carried out with cationic-substituted polysiloxanes and lightfastness agents having carboxylic acid functional groups thereon, such as hydroxybenzoic acids and alkoxybenzoic acids. These carboxylic acids can be obtained from a number of commercial sources. Specifically, salicylic acid, 3-hydroxybenzoic acid, 2,3-dimethoxybenzoic acid, 2,4-dimethoxybenzoic acid, 2,5-dimethoxybenzoic acid, 2,6-dimethoxybenzoic acid, 3,4-dimethoxybenzoic acid, and 3,5-dimethoxybenzoic acid are available from Aldrich Chemical Co., Milwaukee, Wis. 3-(2H-Benzotriazol-2-yl)-4-hydroxyphenylpropionic acid can be synthesized as follows:

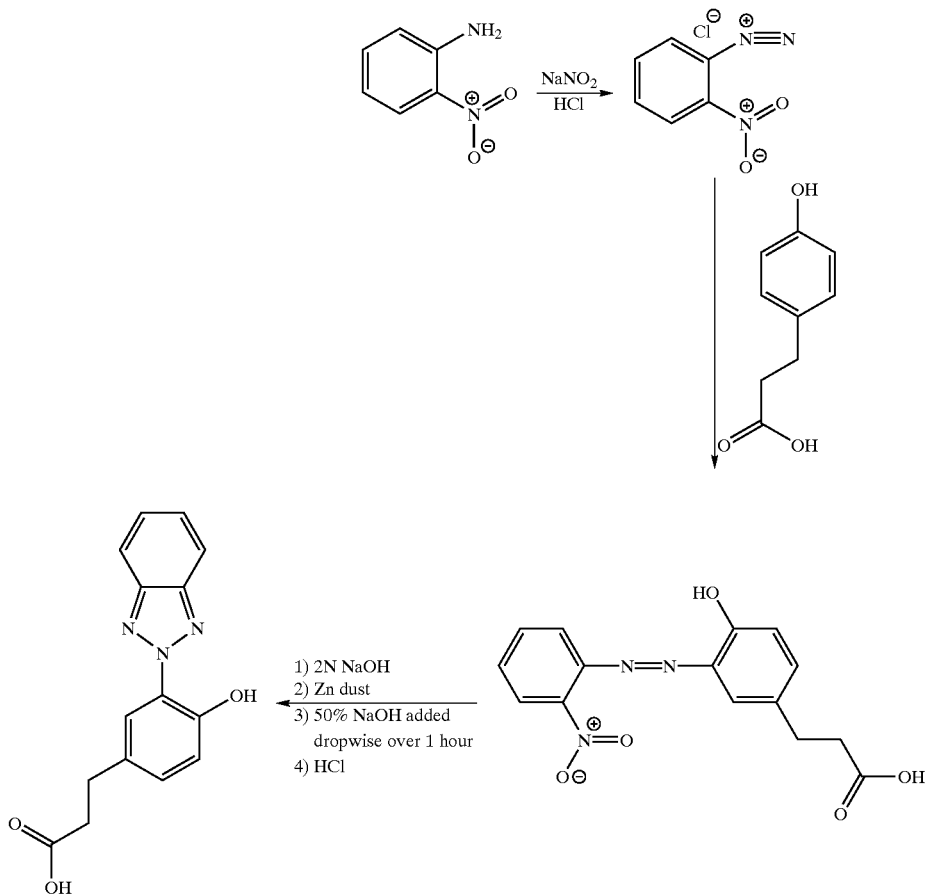

The present invention also includes cosmetic compositions comprising, in a cosmetically acceptable vehicle, carrier, or diluent, the compounds according to the present invention. These cosmetic compositions contain a compound according to the present invention in any desired or effective amount, typically at least about 0.1 percent by weight of the cosmetic composition, and preferably at least about 0.5 percent by weight of the cosmetic composition, and typically no more than about 20 percent by weight of the cosmetic composition, and preferably no more than about 10 percent by weight of the cosmetic composition, although the amount can be outside of these ranges.

The cosmetic compositions of the invention can be used as compositions for protecting the human epidermis or hair against ultraviolet rays, as sunscreen compositions, or as makeup products. These cosmetic compositions can be in forms such as a lotion, a thickened lotion, a gel, a cream, an ointment, a milk, a powder, a solid stick, or the like, and can optionally be packaged as an aerosol, a foam, a mousse, a spray, or the like. When the cosmetic compositions of the invention are used for photoprotection of the hair, they can be formulated as a shampoo, a lotion, a gel or rinse, to be applied before or after shampooing, before or after dyeing or bleaching, before, during or after permanent-waving or straightening of the hair, or as a styling or treatment lotion or gel, a blow-drying or hair-setting lotion or gel, a hair lacquer, a permanent-waving or hair-straightening composition, a composition for dyeing or bleaching the hair, or the like. When the cosmetic compositions of the invention are used as makeup products for the eyelashes, the eyebrows, the skin, or the hair, such as a skin-treatment cream, a foundation, a lipstick, an eye shadow, a blush, an eyeliner, a mascara, a coloring gel, or the like, they can be formulated in solid or pasty, anhydrous or aqueous form, such as oil-in-water or water-in-oil emulsions, suspensions, or gels. The cosmetic compositions can contain the usual cosmetic adjuvants and additives, such as fats and fatty substances, organic solvents, silicones, thickeners, softeners, emollients, complementary sunscreens, anti-foaming agents, moisturizing or hydrating agents, fragrances and perfumes, preservatives, surfactants, fillers, sequestering agents, anionic, cationic, nonionic, or amphoteric polymers or mixtures thereof, propellants, basifying or acidifying agents, colorants, dyes, pigments, or nanopigments, in particular those designed to provide a complementary photoprotective effect by physically blocking out ultraviolet radiation, or any other ingredient customarily used in cosmetics, especially for the production of sunscreen compositions. The cosmetic treatment of the skin or hair to protect same against the deleterious effects of ultraviolet radiation, in particular solar radiation, comprises topically applying to the skin or hair an effective amount of a sunscreen/cosmetic composition as described above, or of a compound according to the present invention.

Other known components can also be included in the cosmetic compositions of the present invention, including (but not limited to) components such as those disclosed in U.S. Pat. No. 5,610,257, U.S. Pat. No. 5,089,250, U.S. Pat. No. 6,306,411, U.S. Pat. No. 6,306,409, U.S. Pat. No. 6,306,384, U.S. Pat. No. 6,303,656, U.S. Pat. No. 6,299,891, U.S. Pat. No. 6,299,890, U.S. Pat. No. 6,299,866, U.S. Pat. No. 6,299,864, U.S. Pat. No. 6,297,203, U.S. Pat. No. 6,296,858, U.S. Pat. No. 6,296,835, U.S. Pat. No. 6,294,181, U.S. Pat. No. 6,294,159, and U.S. Pat. No. 6,294,158, the disclosures of each of which are totally incorporated herein by reference.

Specific embodiments of the invention will now be described in detail. These examples are intended to be illustrative, and the invention is not limited to the materials, conditions, or process parameters set forth in these embodiments. All parts and percentages are by weight unless otherwise indicated.

EXAMPLE I

Preparation of the Trimethylsilyl Ester of Propenoic Acid

The trimethylsilyl ester of propenoic acid was prepared by reaction of propenoic acid and hexamethyldisilazane. Thus, 13.3 grams (0.133 mole) of propenoic acid (obtained from Aldrich Chemical Co., Milwaukee, Wis.) was charged to a 100 milliliter round bottomed flask fitted with a condenser, argon purge, rubber serum cap, and magnetic stirring bar. After purging for about 15 minutes, 11.8 grams (0.73 mole) of hexamethyldisilazane (obtained from Aldrich Chemical Co.) was added through the serum cap via syringe. The reaction mixture exothermed, and vigorous outgassing was observed for 15 to 20 minutes. A drop of concentrated sulfuric acid was then added and the reaction mixture was refluxed for 2 hours to drive the reaction to completion. The flask was then fitted with a vacuum-jacketed Vigreux column, distillation head, and condenser with fraction cutter. The product was isolated by distillation and was used in Example II.

EXAMPLE II

Preparation of Poly(dimethylsiloxane-co-methyl (carboxypentanoyl) siloxane)-graft-methoxypolyethylene glycol Poly(dimethylsiloxane-co-methyl (carboxyltrimethylsilylpentanoyl)siloxane)-graft-methoxypolyethylene glycol was prepared by hydrosilylation of a mixture of the trimethylsilylester of propenoic acid (prepared in Example I) and methoxy polyethylene glycol monoallyl ether (Bimax Chemical, Cockeysville Md.) catalyzed by platinum divinyltetramethyl disiloxane complex (SIP 6831.0, obtained from Gelest, Inc., Tullytown Pa.). Thus, 19.8 grams (0.05 equivalents) of poly (dimethylsiloxane-co-methyl hydrogen siloxane) containing 15 to 18 mole percent (MeHSiO) (HMS 151, obtained from Gelest, Inc., Tullytown, Pa.), 3.5 grams (0.035 equivalents) of trimethylsilyl pentenoic acid (0.020 equivalents) of methoxy polyethylene glycol monoallyl ether, and 28 grams of methylene chloride were charged to a 50 milliliter bottle equipped with a magnetic stirring bar. The solution was purged with argon for 15 minutes prior to the introduction of 4 drops of SIP 6831.0. The reaction was allowed to proceed for 4 days at ambient temperature. At this time the reaction was judged to be complete on the basis of the disappearance of the characteristic Si—H infrared band at 2160–2180 $cm^{-1}$. Water was then added to the reaction mixture, and hydrolysis was effected by heating the mixture on a steam cone. The water and methylene chloride were then removed in vacuo. Methylene chloride was added and the resulting solution was passed through a column filled with neutral alumina to remove spent Pt catalyst. Removal of methylene chloride in vacuo yielded the desired product.

EXAMPLE III

Preparation of Poly(dimethylsiloxane-co-methyl(3-propyl(2-hydroxybenzophenone)siloxane)-graft-methoxypolyethylene glycol)

Poly(dimethylsiloxane-co-methyl(3-propyl(2-hydroxybenzophenone) siloxane)-graft-methoxypolyethylene glycol) was prepared by hydrosilylation of a mixture of allyloxyhydroxybenzophenone and methoxy polyethylene glycol monoallyl ether catalyzed by platinum divinyltetramethyl disiloxane complex (SIP 6831.0, obtained from Gelest, Inc., Tullytown Pa.). Thus, 19.8 grams (0.05 equivalents) of poly(dimethylsiloxane-co-methyl hydrogen siloxane) containing 15 to 18 mole percent (MeHSiO) (HMS 151, obtained from Gelest, Inc., Tullytown, Pa.), 0.035 equivalents of allyloxyhydroxybenzophenone, 0.020 equivalents of methoxy polyethylene glycol monoallyl ether, and 28 grams of methylene chloride were charged to a 50 milliliter bottle equipped with a magnetic stirring bar. The solution was purged with argon for 15 minutes prior to the introduction of 4 drops of SIP 6831.0. The reaction was allowed to proceed for 4 days at ambient temperature. At this time the reaction was judged to be complete on the basis of the disappearance of the characteristic Si—H infrared band at 2160–2180 $cm^{-1}$. Additional methylene chloride was added and the resulting solution was passed through a column filled with neutra alumina to remove spent Pt catalyst. Removal of methylene chloride in vacuo yielded the desired product.

EXAMPLE IV

Preparation of Poly(dimethylsiloxane-co-methyl(3-propyl(2-hydroxybenzotriazole)siloxane)-graft-methoxypolyethylene glycol)

Poly(dimethylsiloxane-co-methyl(2-(3-2H-benzotriazol-2-yl)-4-hydroxyphenyl)ethylpentanoate) siloxane)-graft-methoxypolyethylene glycol) was prepared by a procedure analogous to that of Example III except that the allyloxyhydroxybenzophenone was substituted with 2-(3-2H-benzotriazol-2-yl-4-hydroxyphenyl) ethylpentenoate. 2-(3-2H-benzotriazol-2-yl-4-hydroxyphenyl) ethylpentenoate was synthesized by esterification of 2-(3-2H-benzotriazol-2-yl-4-hydroxyphenethyl alcohol (Aldrich 43,071-4) with pentenoic acid (Aldrich 24,592-5) or pentenoic anhydride (Aldrich 47,180-1).

EXAMPLE V

Preparation of Quaternary Ammonium Hydroxybenzotriazole Salt of Poly(dimethylsiloxane-co-methyl (carboxypentanoyl) siloxane)-graft-methoxypolyethylene glycol)

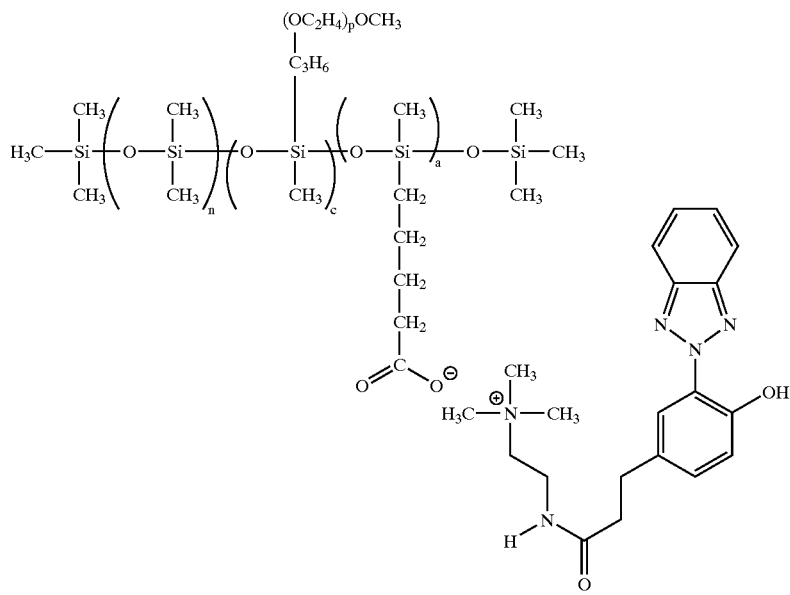

The above complex with a cationic lightfastness agent is prepared by ion exchange. Ion exchange is accomplished by mixing of an acetone solution containing the cationic lightfastness agent in acetone with an acetone solution containing the anionic hydrophilic polysiloxane prepared in Example II. NaCl is removed by filtration and the product is obtained by removal of acetone in vacuo.

EXAMPLE VI

Synthesis of the 2-hydroxy-4-methoxybenzophenone-5-sulfonate salt of QMS 435

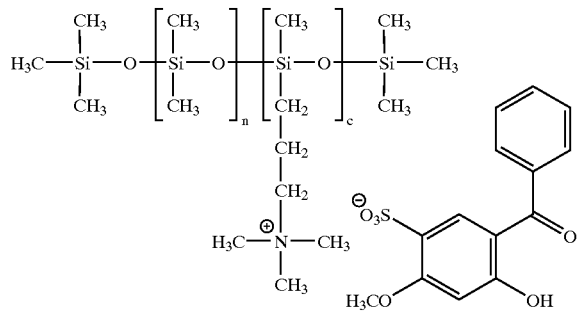

The 2-hydroxy-4-methoxybenzophenone-5-sulfonate salt of QMS 435 (poly(dimethylsiloxane-co-methyl(3-trimethylaminopropyl) siloxane)) is prepared by ion exchange. Ion exchange is accomplished by mixing of an acetone solution containing the anionic lightfastness agent sodium 2-hydroxy-4-methoxybenzophenone-5-sulfonate in acetone with an acetone solution containing the cationic polysiloxane QMS435 (available from Gelest, Inc., Tullytown, Pa.). NaCl is removed by filtration and the product is obtained by removal of acetone in vacuo.

EXAMPLE VII

Sunscreen compositions are prepared by admixing 3 parts by weight of one of the compounds prepared as described in Examples II through VI, 3 parts by weight of oxyethylenated cetylstearyl alcohol (commercially available as MERGITAL CS15 from Henkel), 4.8 parts by weight of glycerol monostearate, 4.5 parts by weight of myristic alcohol, 10 parts by weight of a benzoate of alcohols having 12 to 15 carbon atoms (commercially available as FINSOLV TN from Witco), 6 parts by weight of propylene glycol, 0.2 part by weight of a preservative, 0.6 part by weight of a perfume, and 68 grams of water. The water containing the hydrosoluble compounds is heated to from about 80 to about 85° C., and the oily phase is added to the aqueous phase. After ten minutes of brisk stirring, the mixture is allowed to cool under moderate stirring, followed by addition of the perfume and the preservative. The resulting compositions are useful as sunscreen emulsions.

EXAMPLE VIII

Sunscreen compositions are prepared by heating, admixing, and subsequently cooling 3 parts by weight of one of the compounds prepared as described in Examples II through VI, 20 parts by weight of a hydrocarbonated mineral wax, 7 parts by weight of beeswax, 12 parts by weight of oleic alcohol, 8 parts by weight of hydrogenated lanolin, 8 parts by weight of liquid lanolin, 1 part by weight of carnauba wax, 20 parts by weight of a benzoate of alcohols having 12 to 15 carbon atoms (commercially available as FINSOLV TN from Witco), 1.2 parts by weight of perfume, and 20 parts by weight of VASELINE. The resulting compositions are useful as sunscreen sticks.

EXAMPLE IX

Sunscreen compositions are prepared by admixing 5 parts by weight of one of the compounds prepared as described in Examples II through VI, 7 parts by weight of a mixture of cetylstearyl alcohol and oxyethylenated cetylstearyl alcohol (33 moles ethylene oxide, commercially available as SINNOWAX 10 from Henkel), 2 parts by weight of a mixture of glycerol monostearate and glycerol distearate, 1.5 parts by weight of cetyl alcohol, 15 parts by weight of a benzoate of alcohols having 12 to 15 carbon atoms (commercially available as FINSOLV TN from Witco), 1.5 parts by weight of polydimethylsiloxane, 20 parts by weight of glycerine, 0.2 part by weight of a preservative, 0.6 part by weight of a perfume, and 48 parts by weight of water. The cream is prepared by dissolving the filter in the oily phase containing the emulsionates, heating the oily phase to from about 70 to about 80° C., and adding, under brisk agitation, the water heated to the same temperature. Agitation is maintained for 10 to 15 minutes followed by allowing the mixture to cool under moderate agitation, and at a temperature of about 40° C. the perfume and preservative are added. The resulting compositions are useful as sunscreen creams.

EXAMPLE X

Sunscreen compositions are prepared by admixing 1.4 parts by weight of one of the compounds prepared as described in Examples II through VI and 98.6 parts by weight of a benzoate of alcohols having 12 to 15 carbon atoms (commercially available as FINSOLV TN from Witco). The resulting compositions are useful as hair protection lotions and can be applied to wet hair to protect the dried hair from the sun.

EXAMPLE XI

Sunscreen compositions are prepared by admixing 5 parts by weight of one of the compounds prepared as described in Examples II through VI, 10 parts by weight of ethanol, and 85 parts by weight of $C_8$–$C_{12}$ fatty acid triglycerides (commercially available as MIGLYCOL 812 from Dynamit Nobel). The resulting compositions are useful as hair protection lotions and can be applied to wet hair to protect the dried hair from the sun.

Other embodiments and modifications of the present invention may occur to those of ordinary skill in the art subsequent to a review of the information presented herein; these embodiments and modifications, as well as equivalents thereof, are also included within the scope of this invention.

The recited order of processing elements or sequences, or the use of numbers, letters, or other designations therefor, is not intended to limit a claimed process to any order except as specified in the claim itself.

What is claimed is:

1. A compound of the formula

I

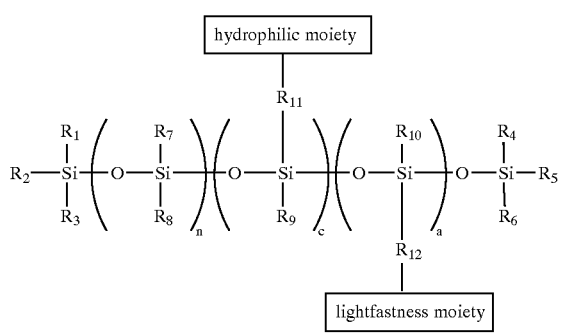

wherein $R_1$, $R_2$, $R_3$, $R_4$, $R_5$, $R_6$, $R_7$, $R_8$, $R_9$, and $R_{10}$ each, independently of the others, is an alkyl group, an aryl group, an arylalkyl group, or an alkylaryl group, $R_{11}$ and $R_{12}$ each, independently of the others, is an alkylene group, an arylene group, an arylalkylene group, or an alkylarylene group, n is an integer representing the number of repeat —OSi($R_7$)($R_8$)— monomer units, a is an integer representing the number of repeat —OSi($R_{10}$)($R_{12}$-lightfastness moiety)— monomer units, and c is an integer representing the number of repeat —OSi($R_9$)($R_{11}$-hydrophilic moiety)— monomer units, wherein the lightfastness moiety is a hydroxybenzophenone group, and wherein the hydrophilic moiety is a polyethylene oxide chain.

2. A compound according to claim 1 wherein the lightfastness moiety is of one of the formulae

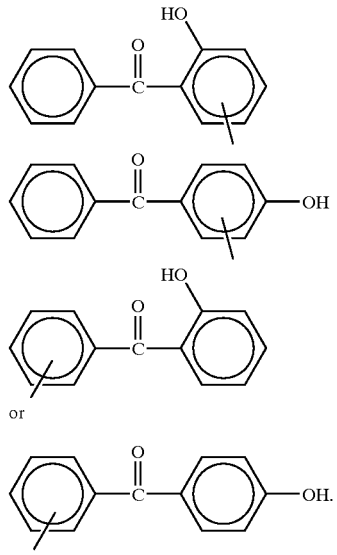

3. A compound according to claim 1 wherein the lightfastness moiety is of the formula

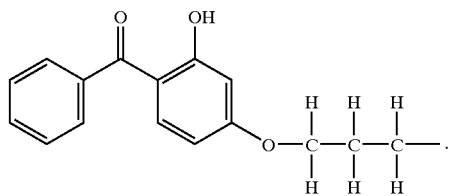

4. A compound according to claim 1 wherein the compound is poly(dimethylsiloxane-co-methyl(3-propyl(2-hydroxybenzophenone) siloxane)-graft-methoxypolyethylene glycol).

5. A compound according to claim 1 wherein n is from about 3 to about 100, a is from 1 to about 20, and c is from 1 to about 50.

6. A compound according to claim 1 wherein n is from about 3 to about 50, a is from 1 to about 10, and c is from 1 to about 20.

7. A compound according to claim 1 wherein n is from about 3 to about 20, a is from 1 to about 5, and c is from 1 to about 10.

8. A compound according to claim 1 having a number average molecular weight of from about 1,000 to about 50,000.

9. A compound according to claim 1 having a number average molecular weight of from about 2,000 to about 20,000.

10. A compound according to claim 1 wherein the polyethylene oxide chain has from 1 to about 60 repeat ethylene oxide units.

11. A compound according to claim 1 wherein the polyethylene oxide chain has from 1 to about 30 repeat ethylene oxide units.

12. A compound according to claim 1 wherein the polyethylene oxide chain has from 1 to about 10 repeat ethylene oxide units.

13. A compound according to claim 1 wherein the polyethylene oxide chain has from about 6 to about 30 repeat ethylene oxide units.

14. A compound according to claim 1 wherein the polyethylene oxide chain has from about 9 to about 20 repeat ethylene oxide units.

* * * * *